(12) United States Patent
Mathur

(10) Patent No.: US 7,953,699 B2
(45) Date of Patent: May 31, 2011

(54) SYSTEM FOR THE PROCESSING OF INFORMATION BETWEEN REMOTELY LOCATED HEALTHCARE ENTITIES

(75) Inventor: Alok Mathur, Alpharetta, GA (US)

(73) Assignee: Medicity, Inc., Salt Lake City, UT (US)

( * ) Notice: Subject to any disclaimer, the term of this patent is extended or adjusted under 35 U.S.C. 154(b) by 0 days.

(21) Appl. No.: 12/630,847

(22) Filed: Dec. 4, 2009

(65) Prior Publication Data

US 2010/0076783 A1   Mar. 25, 2010

Related U.S. Application Data

(63) Continuation of application No. 11/928,783, filed on Oct. 30, 2007, now Pat. No. 7,653,634, which is a continuation-in-part of application No. 11/460,138, filed on Jul. 26, 2004, now abandoned.

(60) Provisional application No. 60/595,668, filed on Jul. 26, 2005, provisional application No. 60/702,686, filed on Jul. 26, 2005.

(51) Int. Cl.
*G06F 17/00* (2006.01)

(52) U.S. Cl. .................. 707/610; 707/609

(58) Field of Classification Search .......... 707/610, 707/609
See application file for complete search history.

(56) References Cited

U.S. PATENT DOCUMENTS

| | | | |
|---|---|---|---|
| 2002/0059257 A1* | 5/2002 | Matsumura et al. | 707/10 |
| 2002/0099273 A1* | 7/2002 | Bocionek et al. | 600/300 |
| 2003/0208382 A1* | 11/2003 | Westfall | 705/3 |
| 2004/0128163 A1* | 7/2004 | Goodman et al. | 705/2 |
| 2004/0249729 A1* | 12/2004 | Matsumura et al. | 705/28 |
| 2005/0071194 A1* | 3/2005 | Bormann et al. | 705/2 |
| 2006/0259324 A1* | 11/2006 | Patterson | 705/2 |
| 2006/0259325 A1* | 11/2006 | Patterson | 705/2 |

* cited by examiner

*Primary Examiner* — Mohammad Ali
*Assistant Examiner* — John P Hocker
(74) *Attorney, Agent, or Firm* — Patent Law Works LLP

(57) ABSTRACT

Systems and methods for reconciling healthcare data between multiple distributed computing nodes that enable an individual node, a topic object, or an intelligent agent to determine synchronization with other nodes, comprising sending source node data to a payload generator, the source node data including difference data, an encapsulated topic object, or intelligent agent communications, generating a payload including the source node data and destination attributes, and sending the payload to a destination node, topic object, or destination intelligent agent, and using the source node data to update destination node data according to destination node, topic object, or destination intelligent agent requirements.

49 Claims, 26 Drawing Sheets

SYSTEM FOR THE PROCESSING OF INFORMATION BETWEEN REMOTELY LOCATED HEALTHCARE ENTITIES

CROSS REFERENCE TO RELATED APPLICATIONS

This application is a continuation of U.S. patent application Ser. No. 11/928,783, which is a continuation-in-part of, and claims the benefit of and priority to, U.S. patent application Ser. No. 11/460,138, entitled "A Distributed Computing System to Enable the Secure Exchange of Information Between Remotely Located Healthcare Applications," filed Jul. 26, 2006, which claims benefit under 35 U.S.C.§119(e) of U.S. Provisional Patent Application Ser. No. 60/595,668, entitled "The Secure Exchange of Information Between Remotely Located Healthcare Applications," filed Jul. 26, 2005, and of U.S. Provisional Patent Application Ser. No. 60/702,686, entitled "The Secure Exchange of Information Between Remotely Located Healthcare Applications," filed Jul. 26, 2005, each of which is incorporated herein by reference as if set forth herein in its entirety.

TECHNICAL FIELD

The present invention relates generally to distributed computing systems, and more particularly, to securely exchanging information between remote computing systems, enabling interoperability and allowing for the synchronization of common information.

BACKGROUND

There is an increasing use of information technology (IT) by physicians as evidenced by the rapid adoption of a type of computer software, called Electronic Medical Records (EMR), to replace the paper charts in the medical office. The use of EMRs by physicians is expected to become common over the next five to ten years.

Because of the state of the art in communications between providers in the healthcare community, most physicians using an EMR must accept or receive data such as lab results, pathology results, radiology results and transcriptions via faxes or paper couriered from the hospital. The physician must then use their personnel to collect the paper fax, scan it into the EMR, and index the scanned image to a particular patient's record. Cumulatively, the process can take several minutes per fax received.

As these computer systems are adopted, there is an emerging need to receive data from hospitals in an electronic format that can be directly interfaced into the physician EMR. Data standards like ANSI's Health Level 7 (HL7) have evolved to address this need and are used by both hospital and physician-based computer systems.

However, the detailed use of the HL7 standard varies between vendors. This is a well-known problem that led to the emergence of a type of middleware called an "interface engine." Its purpose was to translate the HL7 messages exchanged between computer systems into the native format of each. This enabled the computer systems to off-load the responsibility of managing each individual interface. Instead, each computer system would only need to manage its connection to the interface engine.

While the interface engines and EAI middleware offer advantages in enterprise settings where all computer systems are accessible via a local area network, the situation presented by EMRs is more complex.

EMRs are installed in remote physician practices, are unreachable by computer systems located in hospitals, and support the type of data that tends to be highly confidential and must be secured in the most rigorous manner.

As a result, approaches that leverage middleware technologies like HL7 interface engines must devise their own methods of delivering and securing the data. Several of the approaches currently available are: (1) establish a private network between the hospital and the EMR location, (2) use secure email to deliver the electronic data as an attachment, (3) send the electronic data via a secure website where it can be downloaded and (4) use peer-to-peer technology to enable file sharing.

Each of these approaches has the benefit of leveraging existing technology (e.g. email, web, P2P) and does accomplish the overall goal of getting electronic data from the hospital into the remote EMR. However, there are drawbacks with each approach, such as: (1) building private networks is expensive and difficult to manage as volume rises, and (2) secure email, web and P2P solutions rely on people to run the communication application, e.g., open the email, access the website or pull down the data over the P2P network.

Consequently, a need exists for allowing the electronic data to flow from system to system without involving personnel, or a special network or interface for each remote system encountered.

The preferred embodiment defined herein describes such a system that exhibits characteristics of low cost, simple operation, ease of use, reliability and stability in real-world implementations of the embodiment.

SUMMARY

In response to these and other shortcomings of the prior art, the present invention provides systems and methods for securely exchanging information between remote computing systems such as electronic medical records (EMR) in the local healthcare community, enabling interoperability and allowing for the synchronization of common information. One embodiment provides a method for reconciling healthcare data between multiple distributed computing nodes that enables an individual node to determine the portion of overlap data to be synchronized with other nodes and comprises: at a source node with source node data that includes difference data sending the source node data to generate a payload at a payload generator, wherein the payload includes the source node data and destination attributes, saving the payload in a rendezvous queue, and streaming the payload into a rendezvous payload processor; determining a destination node from the destination attributes, and putting the payload into a destination node queue corresponding to the destination node; downloading the payload to the destination node; and processing the payload, using the source node data to update destination node data, according to destination node requirements, wherein specified portions of the destination node data are reconciled with corresponding portions of the source node data.

Another embodiment provides a method for reconciling healthcare data between multiple distributed computing nodes that enables an individual node to determine the portion of data to be synchronized with other nodes comprising: at a source node data that includes difference data associated with the source node, generating a payload that includes the source node data and destination attributes, and streaming the payload into a rendezvous payload processor; determining a destination node from the destination attributes, and putting the payload into a destination node queue; downloading the payload to the destination node, and processing the payload, to update destination node data, according to destination node requirements, wherein specified portions of the destination node data are reconciled with corresponding portions of the source node data.

Another embodiment provides a method for reconciling healthcare data between multiple distributed computing nodes that enables an individual node to determine synchronization with other nodes, comprising: installing a primary node at a local site, with the primary node configured as a command center, installing a plurality of secondary nodes remote from the primary node, wherein each secondary node is configured to be controlled by the command center and to provide secondary node data that includes difference data associated with that secondary node; configuring a rendezvous server to receive the secondary node data and determine at least one destination node, and placing the secondary node data into the corresponding destination node queue; and the destination node retrieving the secondary node data from the destination node queue, and updating destination node data, according to destination node requirements, wherein specified portions of the destination node data are reconciled with corresponding portions of the secondary node data.

Another embodiment provides a computer implemented method for reconciling healthcare data between multiple distributed computing nodes that enables an individual node to determine the portion of overlap data to be synchronized with other nodes, comprising: at a source node module having data that includes difference data associated with the source node, sending the source node data to a payload generating module, for generating a payload that includes the source node data and destination attributes, and streaming the payload into a rendezvous payload processing module; determining a destination node from the destination attributes, and putting the payload into a destination node queue corresponding to the destination node; and downloading the payload from the destination node queue to the destination node, and processing the payload using the source node data to update destination node data, according to destination node requirements, wherein specified portions of the destination node data are reconciled with corresponding portions of the source node data.

Another embodiment provides a system for reconciling healthcare data between multiple distributed computing nodes that enables an individual node to determine the portion of overlap data to be synchronized with other nodes, comprising: a first node comprising: a first intelligent agent configured to process first node data that includes difference data associated with the first node, a payload generator configured to receive the first node data from the first intelligent agent, encrypt the first node data, add destination attributes, and create a payload, a rendezvous queue for short term storage of the payload, and an upload module configured for streaming the payload; a rendezvous server comprising: a plurality of destination node queues corresponding to separate destination nodes, and a rendezvous payload processor configured to receive payloads from the upload module, determine a destination node from the destination attributes and place the payload in a destination node queue corresponding to the destination node; and secondary nodes comprising: a download module to download the payload from the destination node queue upon determination that the rendezvous server contains the payload, an inbox module to receive the payload from the download module, an inbox sort module to extract the first node data from the payload in the inbox module and decrypt the first node data, and a secondary intelligent agent to receive the first node data from the inbox sort module and update secondary node data according to secondary node requirements, wherein specified portions of the secondary node data are reconciled with corresponding portions of the first node data.

Yet another embodiment provides a method for reconciling healthcare data between multiple distributed computing nodes that enables topic objects to determine the portion of overlap data to be synchronized with other nodes, comprising: at a source node data that includes difference data associated with the source node, streaming the source node data into capsule objects, assembling the capsule objects into at least one topic object; storing the topic objects in a local data store, encapsulating the topic object into a payload, including a payload ID, a payload type, a topic participant list to indicate participant nodes that are allowed access to the topic object, a processor ID, a payload key, and the topic object, encrypting the payload, and sending the payload to a rendezvous server; placing the payload into at least one destination node queue, as identified in the topic participant list; and at the destination node, retrieving the payload from the destination node queue, decrypting the payload, upon a determination that the destination node has access to the topic object, extracting the topic object from the payload, extracting the capsule objects from the topic object, and processing the capsule objects to update destination node data, according to topic object requirements, wherein specified portions of the destination node data are reconciled with corresponding portions of the source node data.

Another embodiment provides a method for reconciling healthcare data between multiple distributed computing nodes that enables topic objects to determine the portion of overlap data to be synchronized with other nodes, comprising: at a source node having data that includes difference data associated with the source node, streaming the source node data into at least one topic object, storing the topic object in a local data store, encapsulating the topic object into a payload, that includes a participant list to indicate participant nodes that are allowed access to the topic object, and the topic object, encrypting the payload, and sending the payload to a destination node as identified in the participant list; and at the destination node: decrypting the payload, upon a determination that the destination node has access to the topic object, extracting the topic object from the payload, and processing the topic object to update destination node data, according to topic object requirements, wherein specified portions of the destination node data are reconciled with corresponding portions of the source node data.

Another embodiment provides a method for reconciling healthcare data between multiple distributed computing nodes that enables topic objects to determine the portion of overlap data to be synchronized with other nodes, comprising: at a source node having source node data that includes difference data associated with the source node, serializing the source node data into a topic object, defining a topic participant list to include at least one participant node related to the topic object, wherein the participant node is deemed by the topic object to have a need for access to the topic object, encapsulating the topic participant list into the topic object, storing the topic object at the source node, sending the topic object to the participant node; and at the participant node, processing the topic object, wherein the processing is according to topic object requirements so that specified portions of participant node data are reconciled with corresponding portions of the source node data.

Another embodiment provides a computer-implemented method for reconciling healthcare data between multiple distributed computing nodes that enables topic objects to determine the portion of overlap data to be synchronized with other nodes, comprising: at a source node module, having source node data that includes difference data associated with the source node: streaming the source node data into capsule objects, assembling the capsule objects into at least one topic object, storing the topic object in a local data store, encapsulating the topic object into a payload, the payload including a payload ID, a payload type, a topic participant list to indicate participant nodes that are allowed access to each topic object, a processor ID, a payload key, and the topic object, encrypting the payload, and sending the payload to a rendezvous server; placing the payload into at least one destination node queue, as identified in the topic participant list; at a destination node module: retrieving the payload from the destination node queue, decrypting the payload, upon a determination that the destination node has access to the topic object, extracting the topic object from the payload, extracting the capsule objects from the topic object, and processing the capsule objects to update destination node data, according to topic object requirements, wherein specified portions of the destination node data are reconciled with corresponding portions of the source node data.

Another embodiment provides a system for reconciling healthcare data between multiple distributed computing nodes that enables topic objects to determine the portion of overlap data to be synchronized with other nodes, comprising: a source node having data that includes difference data associated with the source node, a rendezvous server having at least one destination node queue, at least one destination node, and a local data store, wherein the source node is configured for: streaming the source node data into at least one topic object, storing the at least one topic object in the local data store, encapsulating the at least one topic object into a payload, the payload including a payload ID, a payload type, a topic participant list to indicate participant nodes that are allowed access to each at least one topic object, a processor ID, a payload key, and the at least one topic object, encrypting the payload, and sending the payload to the rendezvous server; wherein the rendezvous server is configured for: placing the payload into the at least one destination node queue, as identified in the topic participant list and corresponding to a destination node; and wherein the destination node is configured for: retrieving the payload from the destination node queue, decrypting the payload, upon a determination that the destination node has access to the topic object, extracting the topic object from the payload; and processing the topic object to update destination node data, according to topic object requirements, wherein specified portions of the destination node data are reconciled with corresponding portions of the source node data.

Yet another embodiment provides a method for reconciling healthcare data between multiple distributed computing nodes that enables an intelligent agent to interact with applications, users, and other intelligent agents, to determine portions of the healthcare data to be synchronized with other nodes, comprising: at a source intelligent agent within a source node, having an application: receiving the source node data from the application, analyzing the source node data for destination attributes, creating a payload that includes the source node data and the destination attributes, and streaming the payload into a rendezvous payload processor; at the rendezvous payload processor: determining a destination node from the destination attributes, and putting the payload into a destination node queue; at a destination node having a destination intelligent agent: downloading the payload from the destination node queue to the destination node, processing the payload for determination of the destination intelligent agent, and distributing the source node data to the destination intelligent agent, and at the destination intelligent agent: analyzing the source node data for determination of at least one destination action, and performing the destination action.

Another embodiment provides for reconciling healthcare data between multiple distributed computing nodes that enables an intelligent agent to interact with applications, users, and other intelligent agents to determine portions of the healthcare data to be synchronized with other nodes, comprising: at a source intelligent agent: receiving source node data from a source node application, analyzing the source node data for determination of a destination intelligent agent, creating a payload that includes the source node data, and distributing the payload to the destination intelligent agent; and at the destination intelligent agent: processing the payload for determination of the source node data, analyzing the source node data for determination of at least one destination action, and performing the at least one destination action, according to destination intelligent agent requirements, and in collaboration with the source node data.

Another embodiment provides for reconciling healthcare data between multiple distributed computing nodes that enables an intelligent agent to interact with applications, users, and other intelligent agents and determine portions of the healthcare data to be synchronized with other nodes, comprising: at a source intelligent agent within a source node, having a source node application: receiving the source node data from the source node application, wherein the source node data includes: difference data that is associated with the source node, a source user input associated with a source user application, and source application data; analyzing the source node data for determination of destination attributes, creating a payload that includes the source node data and the destination attributes, and streaming the payload into a rendezvous payload processor; at the rendezvous payload processor: determining a destination node from the destination attributes, and putting the payload into a destination node queue; at a destination node having a destination intelligent agent: downloading the payload from the destination node queue to the destination node, processing the payload for determination of the destination intelligent agent, and distributing the source node data to the destination intelligent agent; and at the destination intelligent agent: analyzing the source node data for determination of at least one destination action, and performing the at least one destination action, according to destination intelligent agent requirements, and in collaboration with the source node data.

Another embodiment provides a computer-implemented method for reconciling healthcare data between multiple distributed computing nodes that enables an intelligent agent to interact with applications, users, and other intelligent agents to determine portions of the healthcare data to be synchronized with other nodes, comprising: at a module for a source intelligent agent within a source node having a source node application: receiving the source node data from the source node application, analyzing the source node data for destination attributes, creating a payload that includes the source node data and the destination attributes, and streaming the payload into a rendezvous payload processor module; at the rendezvous payload processor module: determining a destination node from the destination attributes, and putting the payload into a destination node queue; at a destination node module having a destination intelligent agent: downloading the payload from the destination node queue to the destination node, processing the payload for determination of the destination intelligent agent, and distributing the source node data to the destination intelligent agent; and at a destination intelligent agent module: analyzing the source node data for determination of at least one destination action, and performing the at least one destination action.

Another embodiment provides a system for reconciling healthcare data between multiple distributed computing nodes that enables an intelligent agent to interact with applications, users, and other intelligent agents to determine portions of the healthcare data to be synchronized with other nodes, the system comprising: a source intelligent agent at a source node, a rendezvous server, and a destination intelligent agent, wherein the source intelligent agent is configured to: receive source node data from a source application, wherein the source node data includes: difference data that is associated with the source node, a source user input associated with a source user application, and source application data; determine destination attributes for the source node data, create a payload including the source node data and destination attributes, and stream the payload to the rendezvous server; and wherein the rendezvous server is configured to: examine the destination attributes for determination of a destination node, and place the payload in a destination node queue corresponding to the destination node; and wherein the destination node is configured to download the payload from the destination node queue, process the payload for determination of the destination intelligent agent, and distribute the source node data to the destination intelligent agent; and wherein the destination intelligent agent is configured to: analyze the source node data for determination of at least one destination action, and perform the destination action, according to destination intelligent agent requirements, and in collaboration with the source node data.

Other systems, methods, features and advantages of the present invention will be or become apparent to one with skill in the art upon examination of the following drawings and detailed description. It is intended that all such additional systems, methods, features and advantages be included within this description and be within the scope of the present disclosure.

BRIEF DESCRIPTION OF THE DRAWINGS

Many aspects of the invention can be better understood with reference to the following drawings. The components in the drawings are not necessarily to scale, emphasis instead being placed upon clearly illustrating the principles of the present invention. Moreover, in the drawings, like reference numerals designate corresponding parts throughout the several views.

DETAILED DESCRIPTION

Figure 1:
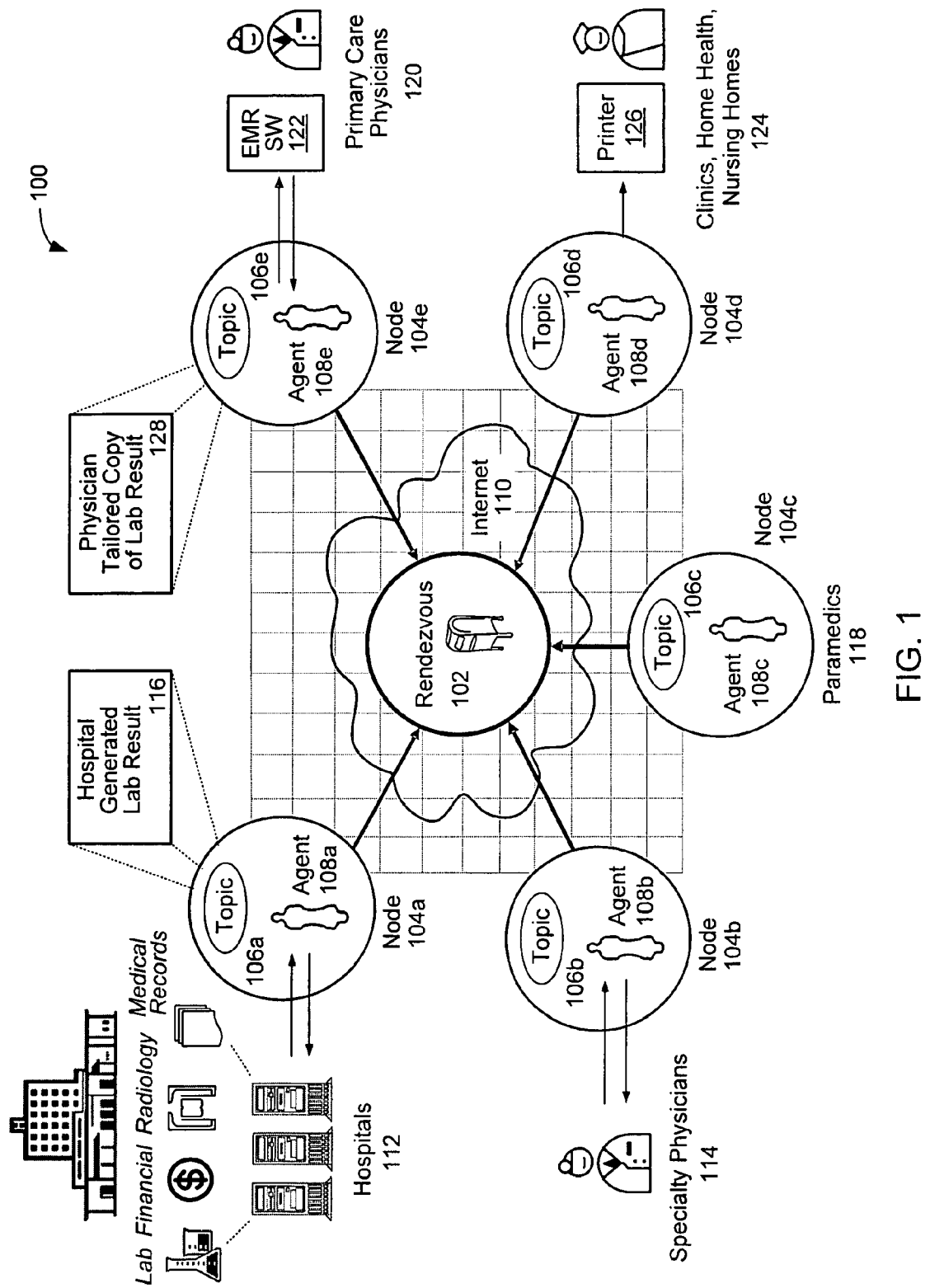
FIG. 1 is an overview of a distributed computing system for reconciling healthcare data between remotely located computing systems.

Reference is now made in detail to the description of the embodiments as illustrated in the drawings. The invention may, however, be embodied in many different forms and should not be construed as limited to the embodiments set forth herein; rather, these embodiments are intended to convey the scope of the invention to those skilled in the art. Furthermore, all "examples" given herein are intended to be non-limiting.

The present invention provides systems and methods for a distributed computing system for securely exchanging information between remote computing systems such as electronic medical records (EMR) in the local healthcare community, enabling interoperability and allowing for the synchronization of common information.

Prior to a detailed description of the invention(s), the following definitions are provided as an aid to understanding the subject matter and terminology of aspects of the present invention(s), are exemplary, and not necessarily limiting of the invention(s), which are expressed in the claims. Whether or not a term is capitalized is not considered definitive or limiting of the meaning of a term. As used in this document, a capitalized term shall have the same meaning as an uncapitalized term, unless the context of the usage specifically indicates that a more restrictive meaning for the capitalized term is intended. A capitalized term within the glossary usually indicates that the capitalized term has a separate definition within the glossary. However, the capitalization or lack thereof within the remainder of this document is not intended to be necessarily limiting unless the context clearly indicates that such limitation is intended.

Access rights: the ability of a user or group of user to access a system, a portion of a system, or individual files within the system. Computer systems control the ability of the users affected to view or make changes to the contents of the system. Based on access rights certain parts of a document may be hidden or non-editable.

Agents: intelligent software programs that are deployed to remote locations to interact with applications and/or users, perform tasks, and collaborate with other agents over the grid.

Application: a computer program that operates on a computer system, e.g. including, but not limited to, a computer program operated on an enterprise computing system, or a user's computer or workstation. Further examples of applications include programs that perform a search in a database, receive and store information in a temporary memory, display selected information on a display screen, etc., and virtually any other type of program.

Command agent: agent configured to execute commands issued from the master node.

Command central: process allowing system administrators to manage remote nodes and agents from a central location.

Electronic medical record (EMR): computer software containing office specific patient clinical and demographic information stored in an electronic format and that replaces paper charts in a medical office. This information may differ across healthcare providers.

Electronic medical record software: computer software containing healthcare provider specific EMRs.

File format: A format or arrangement for encoding information in a digital file that can be stored in, utilized in, or communicated between, computer systems. Each different type of file has a different file format. The file format specifies first a type of the file (e.g. whether the file is a binary file or ASCII file or XML file), and second, how the information is organized in the file into various components and how those components are identified and may be utilized.

Grid architecture: an information grid that distributes and synchronizes information between computers running node software. Agents, running on the nodes, interface to local applications or users and use the grid to collaborate with other agents.

Inbox: queue for storing payloads received from a rendezvous.

Inbox sorter: decrypts payloads and passes them to the receiving agent.

I/O: input/output.

LAN: local-area network, a collection of computers that are connected for electronic communications, typically located geographically close together (that is, in the same building).

Maintenance: administrative utilities to administer the nodes and the agents.

Master node: the command center of the grid. It allows administrators to generate, deploy and activate agents and nodes. It also supports administrative tools and utilities, enabling remote management of the entire system.

Network: a connection for communicating between computers or computer systems. A network usually involves at least two devices capable of being networked together with at least one device usually being a computer. The devices can be geographically close together (LAN) or geographically diverse (Internet).

Node: an operating platform for agents that enable agents to store, distribute and manage information over the grid.

Node warehouse: provides locally persisted information about other nodes on a grid.

Payload generator: creates and equips payloads for delivery.

Protocol: A set of formal rules describing how to transmit data, especially across a network. Low level protocols define the electrical and physical standards to be observed, bit- and byte-ordering and the transmission and error detection and correction of the bit stream. High level protocols deal with the data formatting, including the syntax of messages, the terminal to computer dialogue, character sets, sequencing of messages etc.

Rendezvous: an Internet-based service that manages the secure exchange of information between nodes.

Rendezvous queue: queue for storing payloads received from a rendezvous.

Topic warehouse: enables information to be persisted using the host computer's file system.

Uploader/Downloader: manages connectivity and communications between the node and the rendezvous.

UI: User Interface. Typically means a software application with which a User interacts for purposes of entering information, obtaining information, or causing functions of an associated system to execute.

WANs: wide-area networks, a collection of computers that are connected for electronic communications, typically where the computers are further apart than a LAN and are connected by telephone lines, fiber optic cables, satellite transmission, or radio waves.

WLAN: wireless local area network, e.g. a technology that is used to connect devices, including mobile devices, laptops, desktop computers, entertainment equipment, etc. through a wireless radio signal. Examples include the known WiFi and WiMAX data communication standards.

Turning attention to the drawings, FIG. 1 shows an overview of a distributed computing system 100 for reconciling healthcare data between remotely located computing systems. The exemplary system 100 illustrates an embodiment for securely exchanging information between remote computing systems, enabling interoperability, and allowing remote nodes 104 the option for reconciliation or synchronization of common information. Sites such as hospitals 112, specialty physicians 114, primary care physicians 120, clinics, home health, nursing homes 124, and paramedics 118, among others, connect to a plurality of nodes 104 through the Internet 110 and/or a local network to a rendezvous 102. The rendezvous 102 could be a server functioning much like a mailbox, for example. The interaction allows each party to provide updates to or receive updates regarding healthcare data such as lab reports, financial arrangements, radiology, medical records or other medical information.

Each node 104, or distributed computing software, operates at a local site such as hospitals 112, specialty physicians 114, primary care physicians 120, clinics, home health, nursing homes 124, paramedics 118, or other locale in need of securely synchronizing local copies of medical records with other copies of the same records. A node 104 will typically operate on a local network behind an Internet firewall and supports agents 108 that enable integration, workflow, storage, management and communications from, for example, a local computer. The local computer directly accesses folders or other interfaces to a local network to utilize an application, and thus provides direct interoperability with other computers and networks from other nodes 104 and locales.

The nodes 104 are typically interconnected through the Internet 110 with a rendezvous 102. The rendezvous 102, which could be a server for example, typically receives data, such as encrypted healthcare data, from a node 104, processes the data, and then arranges for the data to be retrieved by other nodes 104. Nodes 104 typically attempt to access the rendezvous 102 on a regular basis to upload information for distribution to other nodes 104. Nodes 104 also download information from its dedicated location or queue at the rendezvous 102. The downloaded information is typically information that has been sent from other nodes 104 within the system 100.

Topic objects 106 are also typically provided at each node 104. Topic objects 106 can be used for storing and managing information at nodes 104 and remote locations. Topic objects 106 provide attributes and methods for creating, structuring, distributing and synchronizing information between multiple nodes 104. Topic objects 106 may provide, for example, a unique topic identifier and/or a list of nodes that participate in the topic object 106.

At each node 104, intelligent agents 108 may interface to local environments, extract data from a payload, parse the data, analyze the data, and/or transform the data into a desired format. Additionally, agents 108 may create or modify topic objects 106 and securely distribute the topic objects 106 to other nodes 104 via the rendezvous 102.

Intelligent agents 108 are typically software programs that are deployed to remote locations to interact with applications and/or users to perform workflow tasks, and to collaborate with other agents across a distributed computing system grid.

Nodes 104 typically provide an operating platform for agents 108, and enable agents 108 to store, distribute and manage information, such as healthcare information over a distributed computing system grid.

The rendezvous 102 is typically an Internet-based service that manages the secure exchange of information between nodes 104.

In one embodiment, a primary care physician 120 could receive healthcare data such as a physician tailored copy of lab result 128 and other medical records from a hospital generated lab result 116 that is generated by the hospital 112 information system automatically. Further, the information is transferred directly to electronic medical record (EMR) software 122 in a format that is acceptable and compatible with the EMR software 122.

Lab Result Example

The following example is presented in greater detail below in reference to the discussion of FIG. 18 through FIG. 26 and provides an illustration of a common lab result exchange in the invention as described. After a patient has had medical tests performed at a hospital, the lab test results are made available through the system 100. For example, a hospital generated lab result 116 is made available from a hospital 112 to the EMR software 122 of a primary care physician 120 as a physician tailored lab result 128.

In this instance, the primary care physician 120 is typically in a remote office location. In summary form, the lab result flows from the hospital 112 to the agent 108a at node 104a, and the agent 108a creates a topic object 106, with the hospital node 104a and the primary care physician node 104e as participants. Once the EMR software 122 of the primary care physician 120 is determined to be the destination node 104e, the message is transformed into the expected format, and after several steps, the topic object 106 is streamed into a payload 280, encrypted and then uploaded from the node 104a to the rendezvous 102 where it is placed into a node queue 146 corresponding to the EMR software associated with the EMR software 122 at node 104e. Then the payload is downloaded to node 104e, decrypted, and the topic object 106 is extracted as the process is reversed until finally the lab result arrives to the EMR software 122 at the primary care physician 120 remote location.

An ACK is returned from the EMR software 122 to the hospital 112 in the same fashion. In the meantime, the intelligent agents 108 at both locations have collaborated to transform the hospital generated lab result in, for example, an HL7 format to an EMR for the physician. Additionally, results from the test are tailored in a fashion that allows the primary care physician to access the information that is needed for his/her services, while safeguarding confidential or private information. Various portions of the lab result data can typically be structured in one or more topic objects, with each topic object having different groups of participants, some of which overlap while others do not. For certain type lab results, the hospital 112 and the primary care physician 120 are members of a particular participant list. For other type information, such as billing, the hospital 112, the primary care physician 120, and an insurance provider are members of another participant list. Different information can be provided to different parties from the same lab result information.

Figure 2:
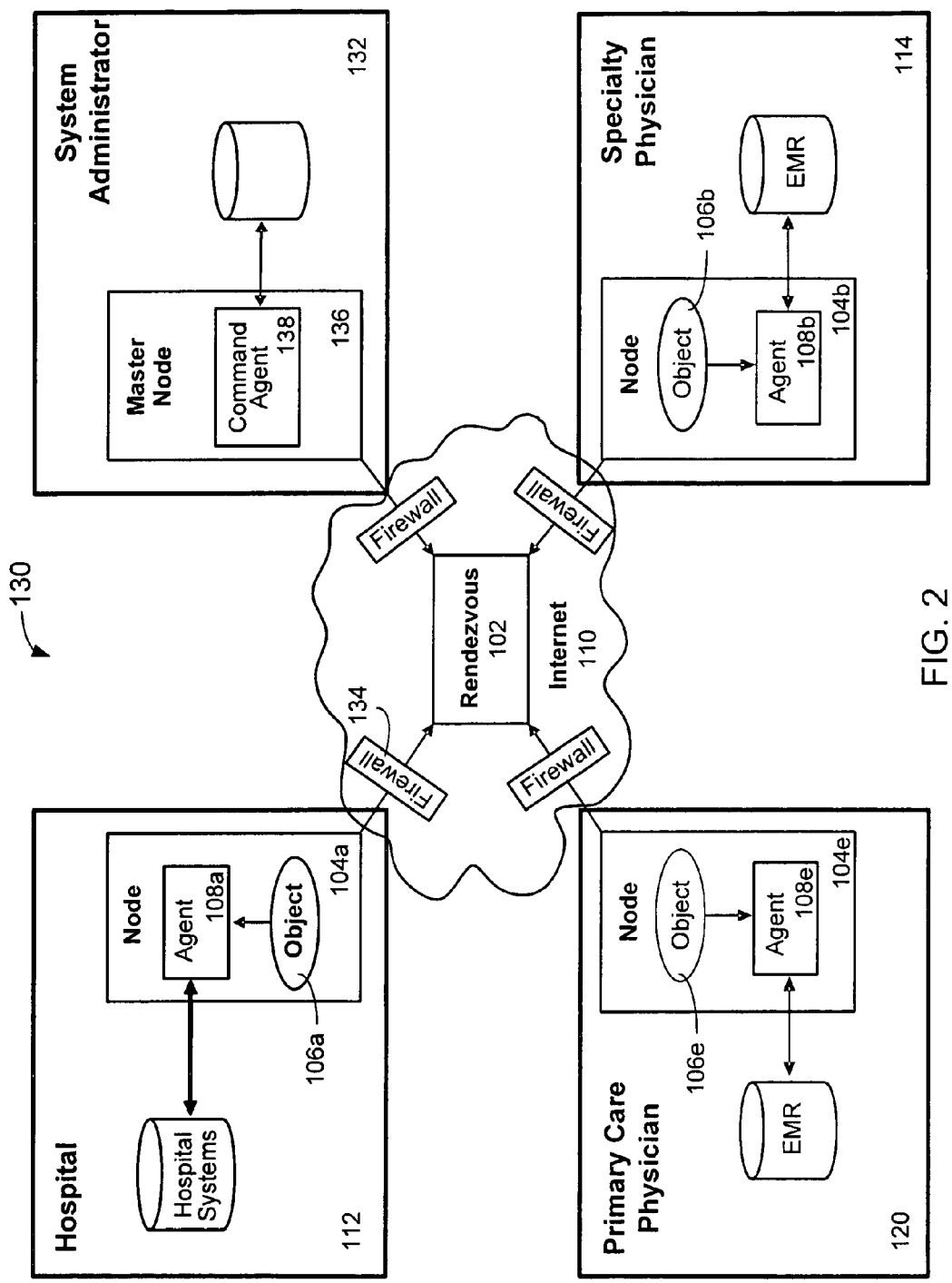
FIG. 2 is a block diagram of an exemplary system derived from the system of FIG. 1.

FIG. 2 is a block diagram of an exemplary system derived from the system of FIG. 1. The exemplary embodiment of a system 130 includes a rendezvous 102, a hospital 112, a specialty physician 114, a primary care physician 120 and a system administrator 132. The nodes 104 (a, b, e) at each local site typically operate behind a firewall 134 and connect to the rendezvous 102 through the Internet 110. Each node 104 (a, b, e) typically contains (1) an application server, (2) a data storage mechanism, (3) a secure communications mechanism, (4) application utilities and methods and (5) management tools and services.

In one embodiment each node 104 (a, b, e) provides for interaction between an intelligent agent 108 (a, b, e) and data, such as a hospital systems database or an EMR, for example. An intelligent agent 108a operating on the node 104a at a hospital 112 could receive healthcare data from a hospital systems database, process the healthcare data and forward the healthcare data to a primary care physician 120 at node 104e and a specialty physician 114 at node 104b awaiting the information. Of course, the number and type of parties receiving the healthcare data would typically be determined at a particular node 104, the hospital 112 in this instance.

In one embodiment, a master node 136, or command center, could operate as a type of system administrator 132 with a command agent 138 for generating, deploying and activating the intelligent agents 108 at the various nodes 104. Multiple intelligent agents 108 may operate at a particular node 104, and multiple nodes 104 may operate at a particular local site.

Figure 3:
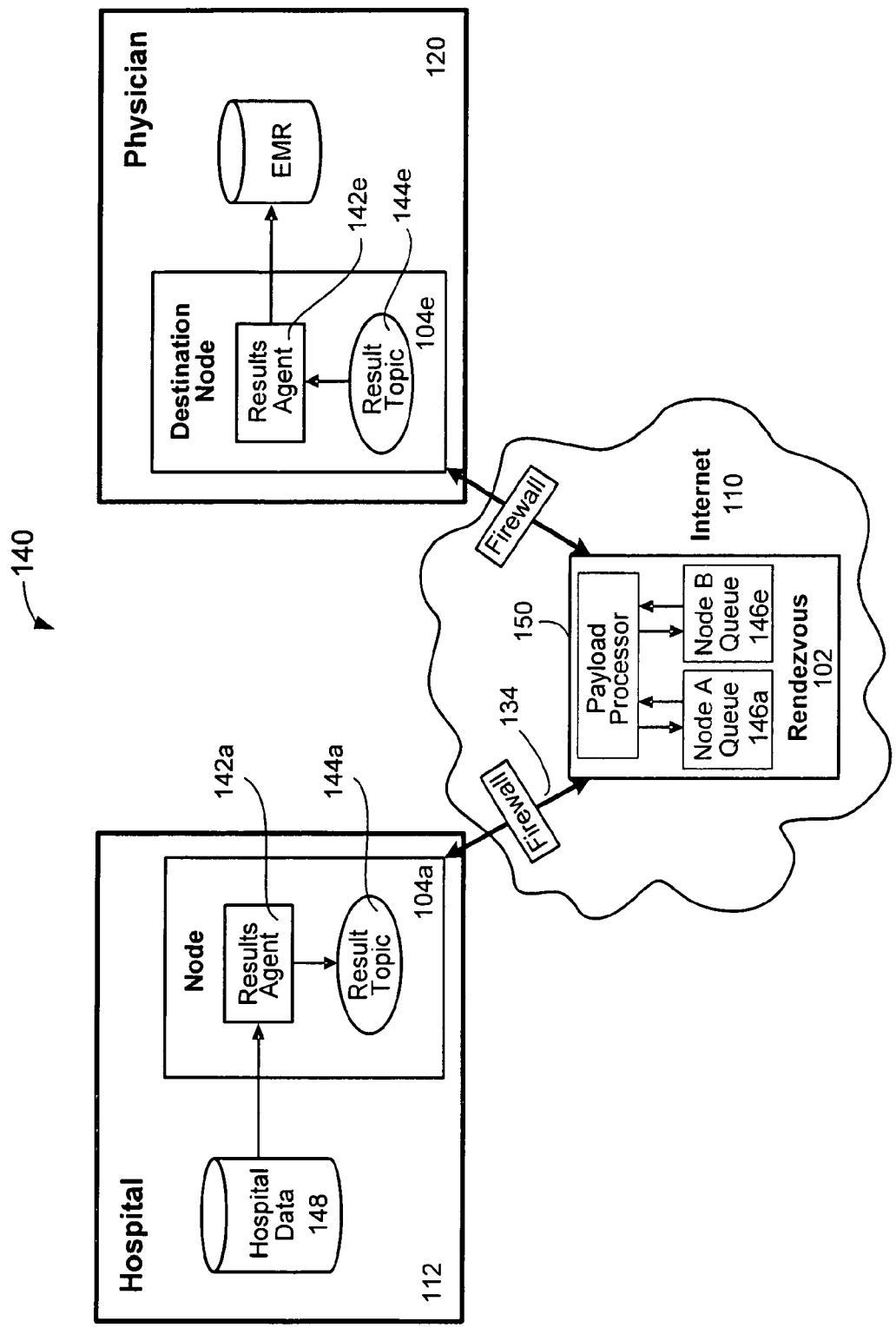
FIG. 3 is a block diagram of an exemplary system for the exchange of electronic information between a primary care physician and a hospital according to the system of FIG. 1.

FIG. 3 illustrates an exemplary embodiment for the exchange of electronic information between a primary care physician and a hospital. The system 140 enables a primary care physician 120 located in a remote office to exchange electronic information such as healthcare data with a hospital 112. Of course, the physician could just as readily exchange electronic information with another physician, a laboratory, or even a patient, for example. A hospital distributes electronic information such as lab test results, lab reports, radiology records, financial records, discharge summaries, medical records, or surgical notes, for example, from among the hospital data to an EMR system located at a doctor's office site such as a primary care physician 120. Healthcare data would typically be distributed utilizing the ANSI Health Level 7 (HL7) data standard, for example. Of course, other appropriate data standards could also be utilized.

Electronic information is automatically received directly into an EMR, in an EMR compatible format, and with no manual intervention necessary. Of course, the information could be received at the doctor's office of the primary care physician 120, or any other designated site where that particular doctor may have need of access to the information. Further, the primary care physician 120 may just as readily supply electronic information to an EMR located at the hospital 112. It should be understood that the exchange of information could be facilitated involving hospitals, patients, specialty physicians, paramedics, primary care physicians, clinics, home health, nursing homes, insurance companies, or any other party with a need requiring access to that particular type of healthcare data. For example, a patient could have lab test results forwarded from a hospital to their primary care physician, a specialty physician, a second physician and an insurance carrier. Thus, a patient could limit the flow of healthcare information to a select few parties or allow the healthcare information to receive broad distribution amongst many medical parties.

In one embodiment, a node 104a is installed on a computer connected to a local area network (LAN) and behind an Internet firewall 134 at a hospital 112 site. The node 104a supports an intelligent agent such as a results agent 142. The results agent 142 could be connected, for example, via a configurable TCP port to the hospital data systems 148. The results agent 142 monitors the hospital data systems 148 for HL7 messages on the configured ports and then receives and processes the messages.

Received HL7 text string messages are parsed by the results agent 142 into results objects. The results objects are then filtered on the basis of the data values within the HL7 message such as, for example, message type, patient type, and ordering provider, among others. The results agent 142 may further process information according to specified rules, such as:

(1) mapping data from one format to another,
(2) adding information not present in the original HL7,
(3) removing or modifying data from the original HL7, and
(4) discarding duplicates and/or acting on changes in status (e.g., preliminary to final).

After capturing and transforming the HL7 message, the results agent 142 creates a topic object denoted in this instance as a result topic object 144. The HL7 message is streamed into the result topic object 144, and routing and management information are added to the result topic object 144 attributes. The routing and management information includes the destination node 104e, such as a primary care physician 120 office, that the results are intended for and also the intelligent agent 108 to notify when the result topic object 144 reaches the destination node 104e.

After creating and saving the topic object, the results agent 142 initiates distribution of the result topic object 144. The initiation process streams the result topic object 144 into a payload data structure and encrypts it for transmission to the rendezvous 102. A secure session, such as a secure socket layer session, is established within the rendezvous 102 for uploading the payload. The payload could be uploaded, for example, over an HTTP/S protocol.

A payload processor 150 application within the rendezvous 102 receives and examines the payload for determination of the nodes 104 to receive a copy of the payload. A sorter then puts a copy of the payload into the destination node queue 146' corresponding to the destination node 104'.

Each node 104a, 104e regularly connect to the rendezvous 102 to check for new payloads in its respective node queue 146a, 146e. In the exemplary embodiment of FIG. 3, the destination node 104e (at the primary care physician 120 site) checks its node queue, the destination node queue 146e, for new payloads. During the next polling interval, any newly deposited payloads are downloaded, the result topic object 144e is extracted and the results agent 142e at the destination node 104e is notified.

The results agent 142e at the destination node 104e opens the result topic object 144e, extracts the information, analyzes, further transforms the HL7 if necessary, and saves the topic object on the node. The results agent 142e also extracts the HL7 from the result topic object 144e and copies it to the EMR for processing by the EMR's interface logic.

The EMR interface typically issues an HL7 acknowledgment (ACK) message to indicate the status of message processing. The ACK message is deemed critical audit information and is required by a hospital 112 to satisfy security regulations.

The results agent 142e at the destination node 104e monitors for an HL7 ACK message from the EMR. The results agent 142e then opens, parses and examines the HL7 ACK for correlation to a result topic object 144e containing the original HL7 result message. After locating the result topic object 144e, the results agent 142e adds the new HL7 ACK string to the result topic object 144e and distributes the updated portion of the topic.

For distributing a topic object 106, the topic or capsule data is delivered from the agent 108 to the node 104—results agent 142e to node 104e in this instance. The node 104e provides for creating, encrypting, and uploading the payload to the rendezvous 102 as discussed above. The payload processor 150 receives the new payload, examines the attributes to determine the nodes 104 to receive a copy of the payload, and puts a copy of the payload into the appropriate node queue (node queue 146 in this instance).

The original node 104a at the hospital 112 also regularly connects to the rendezvous 102, downloads any payloads from its node queue 146, decrypts the payload and passes it to the results agent 142a identified in the payload attributes. The audit trail needed by the hospital 112 is completed by adding the ACK to the stored copy of the result topic object 144a.

Additionally, a node 104 receiving topic object 106 update information may have the option whether to update healthcare data within local applications and data stores. In other words synchronization may be at the discretion of the receiving node 104. Mechanisms are provided to extract, analyze, transform, secure, distribute, process and insert information from one system to a remote system(s).

Figure 4:
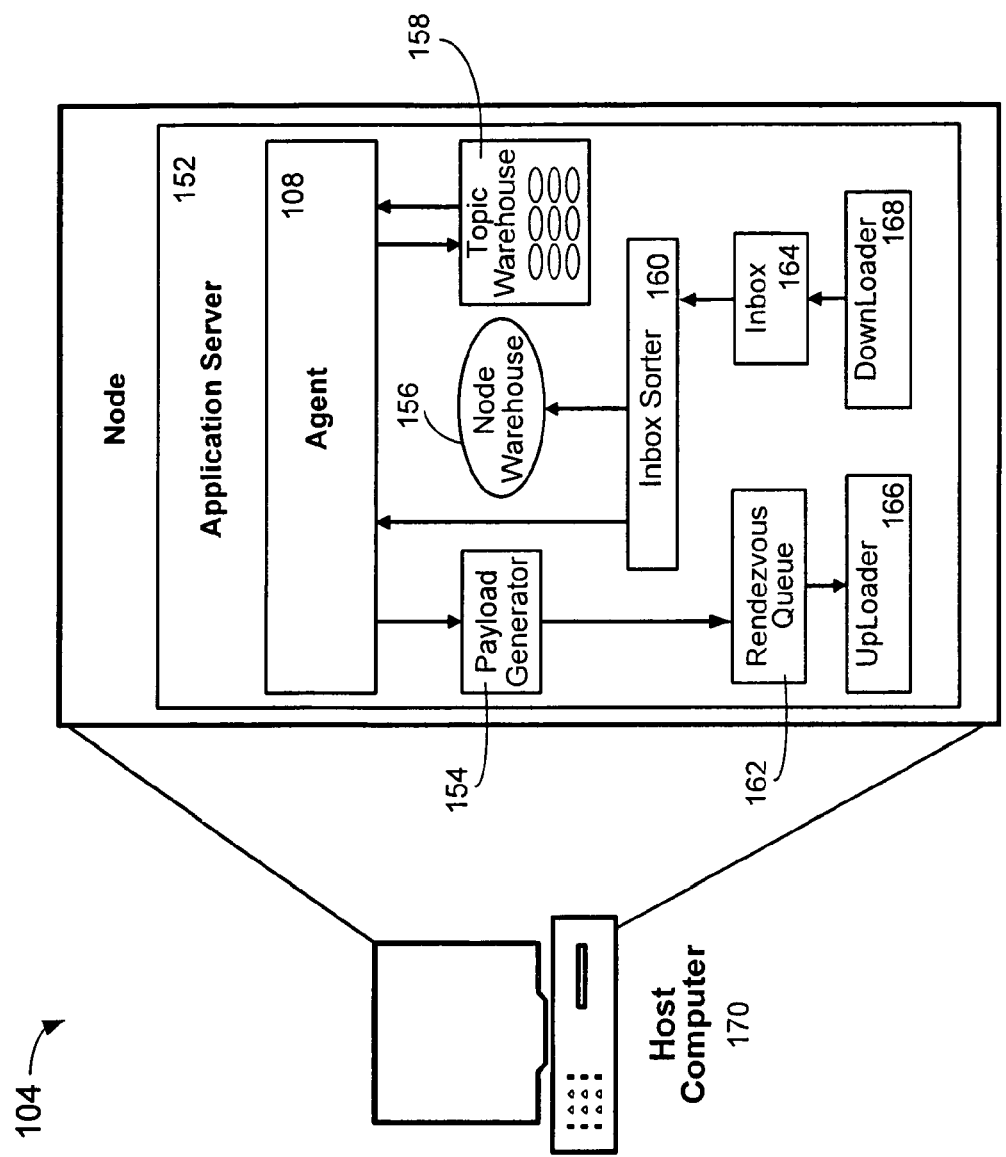
FIG. 4 is a block diagram depicting a node according to the system of FIG. 1.

Each node 104 enables agents 108 to execute in a remote environment, to interface with local systems, and to process and exchange information with other agents 108 located at other nodes 104. Each instance of a node 104 is typically assigned a unique ID and other attributes during initialization. Nodes FIG. 4 illustrates an exemplary embodiment of a node 104 in greater detail. An application server 152 operating on a host computer 170 provides the core functionality of the node 104. The application server 152 provides for compiling and executing node applications.

Agents 108 provide for (1) integration to local applications for processing and exchanging information with other agents 108 on other nodes 104, and (2) management applications allowing the node 104 and agents 108 to be remotely configured and managed.

In addition to the application server 152 and the agent(s) 108, a node 104 typically includes a topic warehouse 158, a node warehouse 156, an uploader 166, a downloader 168, a payload generator 154, an inbox 164, a rendezvous queue 162, an inbox sorter 160, a command module (not shown) and a maintenance module (not shown). The topic warehouse 158 enables information to be persisted using the host computer's 170 file system. The node warehouse 156 provides locally persisted information about other nodes 104. The uploader 166 and downloader 168 manage connectivity and communications between the node 104 and the rendezvous 102. The payload generator 154 creates and encrypts payloads for delivery. An inbox 164 queue is provided for storing payloads received from a rendezvous 102. A rendezvous queue 162 allows for storing payloads waiting to be uploaded to a rendezvous 102. The inbox sorter 160 decrypts payloads and passes them to the receiving agent 108. A command module executes commands received from a master node or command center. A maintenance module provides administrative utilities for administering the node 104 and agents 108. The node 104 functionality provides an operating platform enabling agents 108 to store, distribute and manage information, such as healthcare information over a distributed computing system grid.

The agent 108 utilizes the payload generator 154 to stream topic objects 106 into payloads. Payload attributes are created to identify the destination nodes participating in the topic object 106 and the agents 108 to be evoked when the payload is received at a particular destination node. The payload generator 154 also encrypts payload data using, for example, a combination of symmetric and asymmetric keys that can be decrypted only by a receiving node 104.

Newly created encrypted payloads are placed in a rendezvous queue 162 by the payload generator 154, and are held there for distribution to a server at a rendezvous 102.

Payloads are uploaded from the rendezvous queue 162 to the rendezvous 102 via an uploader 166. The uploader 166 monitors for new payloads in the rendezvous queue on a regular interval. If new payloads are present during the next monitoring interval, they are uploaded to the rendezvous 102. Similarly, payloads are downloaded from the rendezvous server node queue via a downloader 168. The downloader 168 monitors for new payloads in the node queue corresponding to the node 104. If new payloads are present in the node queue, they are downloaded to the node 104. The encrypted payloads retrieved by the downloader 168 are stored in an inbox 164. An inbox sorter 160 processes the payloads from the inbox 164, decrypts payload attributes identifying the agent 108, and then evokes the agent 108.

Additionally, a topic warehouse 158 stores topic objects 106 locally on the node 104. In one example, a topic warehouse class provides methods for use by agents 106 to create, update and remove topic objects 106. Topics are typically stored in a file folder located on the host computer's file system. Thus, nodes 104 may store and participate in many topic objects 106 concurrently—limited only by the host computer storage capacity. Topic objects may also be persisted in databases or other more robust environments as needs dictate.

A node warehouse 156 maintains definition objects for each node 104 registered with the rendezvous 102. The node's definition object includes elements like the unique ID and the public encryption key for the node.

It should be noted that each node 104 generates an asymmetric (public/private) pair of keys at creation for encrypting and decrypting payloads. The node 104 keeps the private key and distributes a copy of its public key via the definition object. The definition object is distributed to all other nodes 104 registered with the rendezvous 102 and stored in their respective node warehouses 156.

The node warehouse 156 is updated upon registration of a new node or modification of an existing node on the rendezvous 102.

The node 104 components operate together to enable an automated exchange process.

Upon creating a topic object 106, the agent 108 utilizes the node warehouse 156 to identify the nodes 104 that participate in the topic. The IDs of the nodes 104 are added to the topic object's 106 attributes and the topic object is passed to the payload generator 154.

Upon sending a topic object 106 to another agent, the agent 108 passes the topic object 106 to the payload generator 154. The topic object attributes include the identification of participating nodes 104, the ID of the sending agent 108, and the ID of the agent to receive the topic object 106.

The payload generator 154 examines the topic attributes to create a new payload. The payload data is encrypted, streamed into the payload, and then the node ID is added to the payload attributes. Upon creating the payload, the payload generator 154 saves the encrypted payload into the rendezvous queue 162.

At a configurable interval, an uploader 166 scans the rendezvous queue 162 for new payloads deposited by the payload generator 154. Upon detecting a new payload, the uploader 166 establishes a secure session with the rendezvous 102 for streaming the payload. The uploader 166 deletes the payload from the rendezvous queue 162 after the rendezvous 102 acknowledges successfully receiving the payload.

A downloader 168 attempts to establish a secure session with the rendezvous 102 at a configurable interval to check for new payloads. Payloads are downloaded and stored in an inbox 164 at the node 104.

The inbox sorter 160 scans the inbox 164 at regular intervals for payloads received from the rendezvous 102. The inbox sorter 160 retrieves payloads from the inbox 164, decrypts the payload using the node's asymmetric private key, examines the payload to determine which agent 108 to invoke, extracts the payload topic data and passes the data to the identified agent 108 for processing.

Rendezvous

Figure 5:
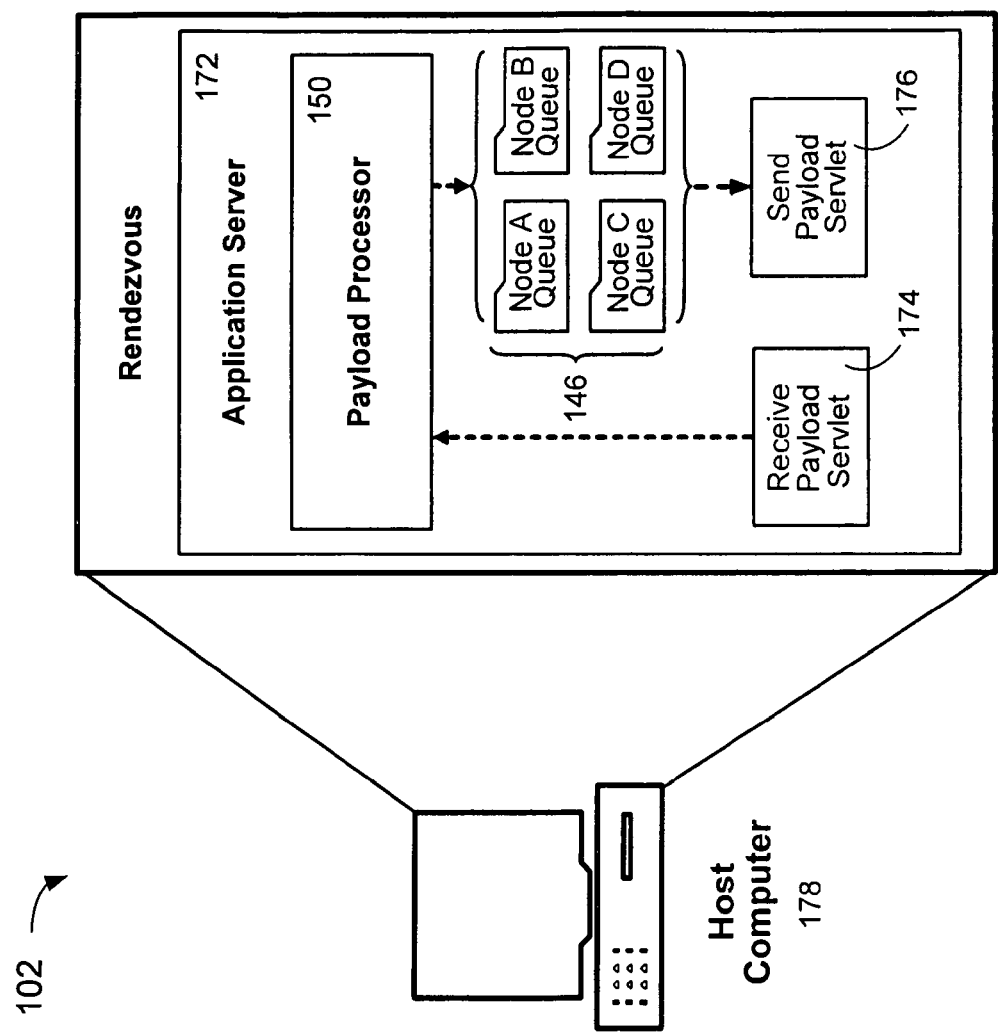
FIG. 5 is a block diagram depicting a rendezvous according to the system of FIG. 1.

FIG. 5 illustrates an exemplary embodiment of a rendezvous 102 in greater detail. A rendezvous 102 is a node that includes the rendezvous server or application on a host computer 178 that is accessible via the Internet 110. The rendezvous 102 manages the exchange of payloads from one node to another, typically over the Internet 110. The rendezvous 102 enables the secure, asynchronous exchange of payloads between nodes 104. All communication with the rendezvous 102 is performed utilizing a secure session, such as the HTTPS protocol. For example, an x.509 security certificate from a recognized certificate authority (CA) is installed on the rendezvous 102 to enable the SSL handshake with an uploader and downloader at each node 104. The rendezvous 102 uses the node's assigned asymmetric private key (discussed in detail below) to authenticate the node 104.

The rendezvous 102 honors requests from recognized (registered) nodes 104 to upload and download payloads.

A rendezvous 102 typically includes a rendezvous application server 172, a payload processor 150, node queues 146, a receive payload servlet 174, and a send payload servlet 176. As in regular nodes 104, the rendezvous 102 also includes a command module (not shown) and a maintenance module (not shown) in addition to grid status management and registration components (both of which are also not shown in FIG. 5). Registration components provide for managing the process of allowing organizations to register for the distributed computing system grid. Grid status management components provide current status regarding node 104 activity across the system.

A node queue 146 is provided for each node 104 that participates on the distributed computing system grid. The embodiment illustrated shows four node queues, depicted as A-D. The node queues 146 are managed by the rendezvous 102. The first exchange of a payload between a node 104 and the rendezvous triggers the rendezvous 102 to generate a unique node queue 146 corresponding to that node 104.

When a node 104 uploads a payload to the rendezvous 102 via its uploader 166, the receive payload servlet 174 is invoked at the rendezvous 102. The receive payload servlet 174 receives payloads over a secure session such as HTTP/S and sends the payloads to the payload processor 150.

The payload processor 150 receives payloads from the receive payload servlet 174 and examines the payload to determine the ID of the nodes 104 listed within the payload. The payload processor 150 places a copy of the payload in the node queue 146 (or destination node queue) corresponding to each of the listed node destinations.

The payload processor 150 also responds to request from nodes 104 to retrieve the payloads from the node queue 146 corresponding to that particular node 104. The send payload servlet 176 responds to the payload requests from a node 104 and downloads the payloads from the node queue 146 corresponding to that node 104.

The rendezvous 102 will typically reside on an Internet accessible server. Further, a rendezvous 102 may be implemented as a single rendezvous configuration, or as multiple redundant rendezvous configurations. Each rendezvous 102 server will typically have an x.509 certificate issued from a well-known CA so that nodes 104 may authenticate the rendezvous 102. Nodes 104 are typically authenticated using system generated PKI keys. Of course, other authentication systems and methods may provide the desired security functionality for the distributed computing system.

Configuration of Multiple Redundant Rendezvous

The configuration of multiple redundant rendezvous servers allows each node 104 to connect through the Internet 110 to each rendezvous 102. Each node 104 also has a node queue 146 on each of the rendezvous 102. Each node 104 has a single inbox 164, but multiple rendezvous queues 162 associated with each rendezvous 102. To prevent duplication of payloads, each node 104 maintains a discard list for each rendezvous 102, indicating the payloads that the node 104 does not require from that particular rendezvous 102.

An example update between two nodes utilizing two rendezvous will serve to illustrate the process. An encrypted payload is created by the payload generator at the first node. A copy of the encrypted payload is placed into both rendezvous queues at the first node. The uploader connects to the first rendezvous and uploads the contents of the first rendezvous queue, and then connects to the second rendezvous and uploads the contents of the second rendezvous queue.

Each rendezvous receives the payload from the uploader, processes the payload, and places it into the appropriate node queue for the destination node.

The downloader at the destination node connects to each rendezvous in turn to download the contents of its node queue. If the initial rendezvous is unavailable, or if the payloads have been received, then the destination node connects with the next rendezvous. After receiving the payload, the destination node updates all discard lists for all rendezvous that match the ID of the received payload.

On the next connection with a rendezvous, the destination node downloader sends the discard list for that rendezvous, and the rendezvous compare the payloads in the destination node queue to the discard list, discarding any payloads from the list that remain in that destination node queue.

The rendezvous returns a list of discarded payloads along with any new payloads to the destination node. Finally, the destination node removes from the corresponding discard list, those payloads that the rendezvous has acknowledged as discarded.

A discard list is exchanged with each communication between a node and a rendezvous, thus eliminating redundant payloads without synchronizing or creating complex interactions and ensuring that only one copy of a payloads is received.

Should a rendezvous fail, the redundancy ensures that the participating nodes continue to download payloads from the other active rendezvous. When the rendezvous again becomes available, the discard list from each node allows for discarding of unwanted payloads.

Topic Objects

Figure 6:
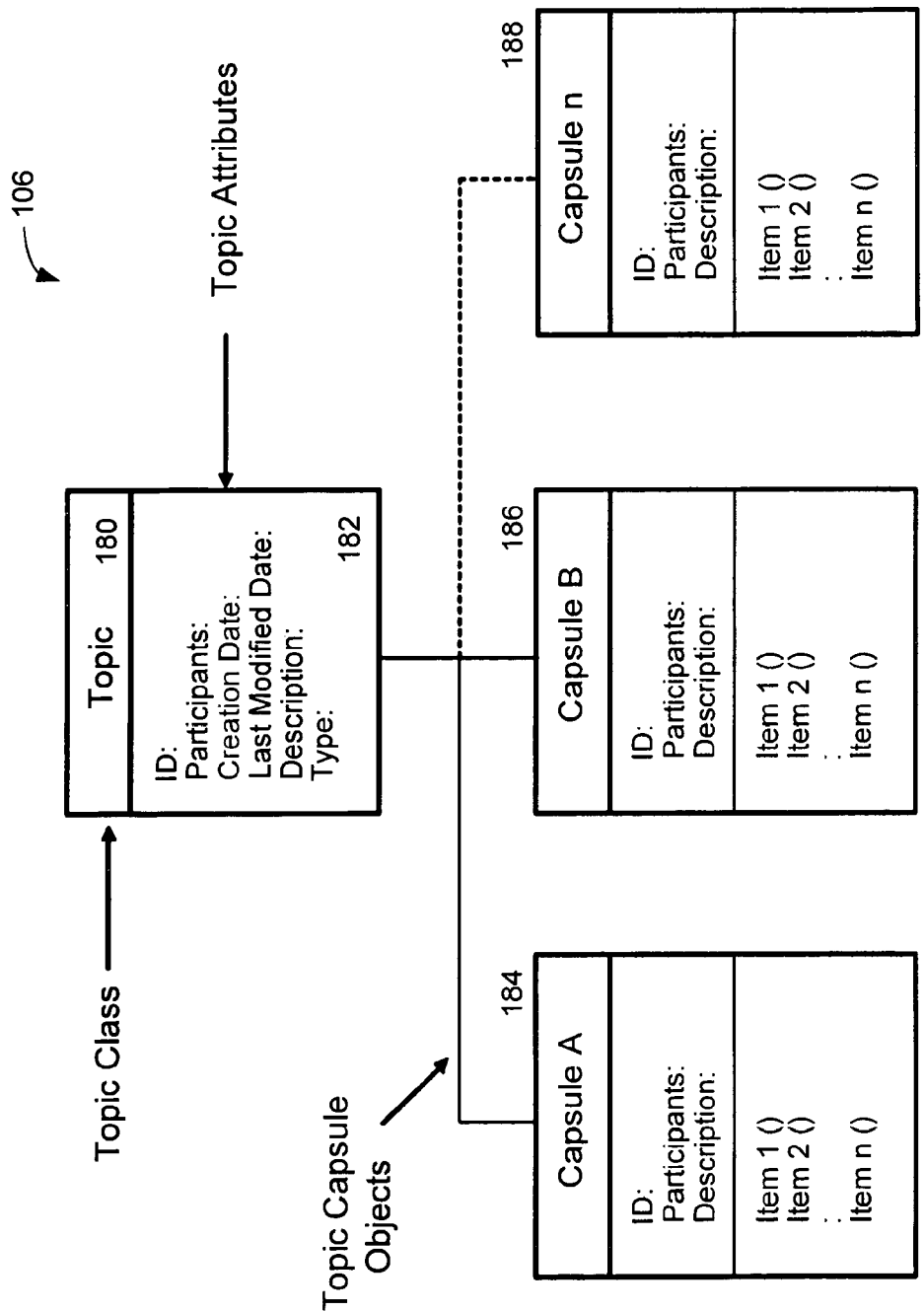
FIG. 6 is a depiction of a topic object class according to the system of FIG. 1.

FIG. 6 illustrates an exemplary embodiment for a topic object 106. Topic objects 106 enable nodes 104 to exchange information related to a topic with other nodes 104. The structure of a topic object 106 allows for creating and distributing copies or replicas of the topic to a plurality of nodes 104, thus allowing the topic to be persisted in each node's respective topic warehouse 158.

A topic object 106 includes the topic class 180, topic attributes 182 within the topic class 180 and topic capsule objects 184, 186, 188. The topic attributes 182 provide a data structure for the information necessary within the system to structure, address and distribute payloads to nodes 104 participating in the topic. Topic attributes 182 include the ID, participants, creation date, last modified date, description and type. The name of the agent that processes the topic, as well as other attributes, can also be included.

A topic object 106 may include multiple topic capsule objects 184, 186, 188 (capsules). Each capsule contains attributes that identify the capsule, including the ID, participants and description. Further, each capsule includes attributes to enable controlling the visibility of topic data between topic participants including methods to create, update, modify and remove data contained in the capsule. One embodiment enables digital information such as, for example, text, digital voice, image, and video, to be streamed into a capsule and distributed between nodes 104 identified as participants in the topic object 106 attributes. It should be noted that the distribution of topic objects 106 to a plurality of nodes 104 allows for an environment where private exchanges between select groups of participants may be enabled.

In one embodiment, a topic could represent a single transaction such as a test result. A result topic could contain the original HL7 message, the HL7 message after being transformed by an agent, the HL7 ACK, an audit history of the topic trail (where the topic went, accessed by whom, etc.) and a list of providers that received the test result (ordering provider, consulting doctor, primary care physician, etc.).

In another embodiment, a topic could represent a medical record, such as a prenatal record. The topic object 106 would contain demographic data on the mother, family history, medical history, lab tests, physical exams and other data aggregated into the prenatal record. The topic could list the OB/GYN, mother, birth center and specialty providers as participants that share the record. When data is added to the prenatal topic, it is immediately and automatically distributed over the distributed computing system grid as a topic object 106 and available to the participants; the need for repeated faxing of the prenatal record is eliminated.

A topic object 106 could be ephemeral, such as a command sent to an agent 108 to perform a maintenance task. After the agent completes the task and reports back, the topic object 106 may be deleted.

Topic objects 106 could also be long lived. For example, a topic object 106 containing a directory of providers on the distributed computing system grid would exist as long as the grid was operational. When a provider joins or leaves the grid, the topic object 106 is updated and distributed to the participants. In this instance, all nodes on the grid would receive the update.

Figure 7:
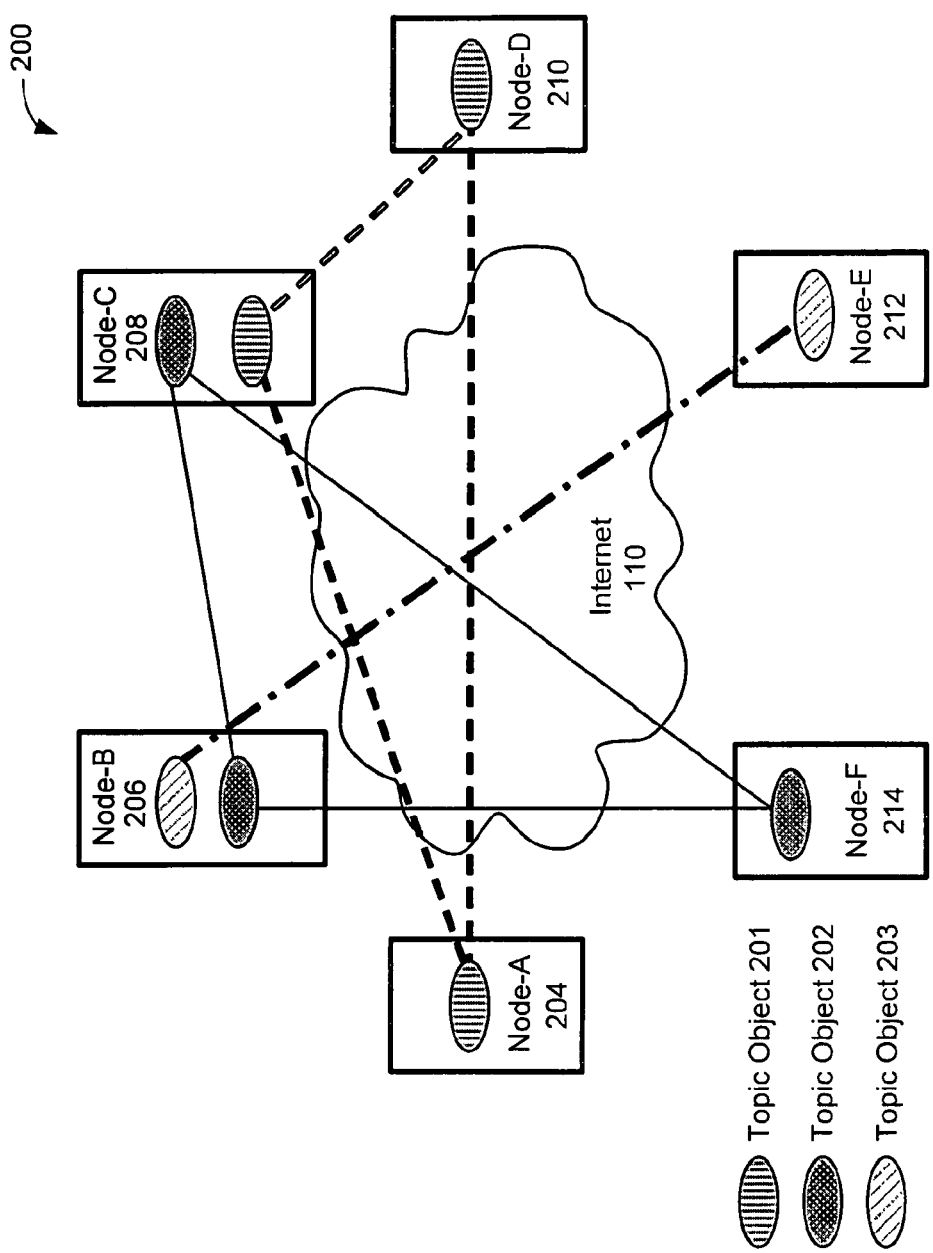
FIG. 7 is topic object participation mapping according to the topic objects of FIG. 6 as utilized in the system of FIG. 1.

FIG. 7 illustrates an exemplary topic participation mapping 200. Topic objects 106 may be distributed across a plurality of nodes 104 to create an environment for private exchange groups within a broader community.

In FIG. 7, six nodes A-F 204, 206, 208, 210, 212 and 214 illustrate a participation mapping among the nodes. The topic warehouse at each node contains the topic objects 106 in which that node participates. Specifically topic object 201 is distributed between node-A 204, node-C 208 and node-D 210. Topic object 202 is distributed between node-B 206, node-C 208 and node-F 214. Topic object 203 is distributed between node-B 206 and node-E 212.

When an agent 108 updates a topic object on a particular node, the agent 108 may initiate the distribution of the updates to other agents 108 participating in the topic object. For example if an agent 108 on node-A 204 updates topic object 201 and initiates distribution of topic object 201, node-C 208 and node-D 210 are automatically updated with the new information upon processing the payloads from the rendezvous 102. Similarly, if an agent 108 on node-D 210 updates topic object 201 and initiates an update, node-A 204 and node-C 208 are automatically updated upon processing the payloads from the rendezvous 102. Thus, node-A 204, node-C 208 and node-D 210 remain synchronized.

In one embodiment of the invention, updating or changing a copy of a topic object can cause the new information to be automatically distributed to all other nodes participating in the topic object. Effectively a virtual object is created, and the state of the virtual object in any one location can match the state of the object in every other location.

Topic objects 106 provide a high degree of privacy. Nodes that participate in a particular topic object have access to the information while nodes that do not participate in that topic object do not have access.

Topic objects 106 have multiple purposes and suit various needs. Three specific topic objects 106 provide for exchange and interoperability between healthcare applications such as EMRs. Result topics provide for exchange of clinical information, provider topics provide a list of physicians that may receive information, and physician office definition topics provide detailed information about a particular physician office, the local physicians and applications.

Figure 8:
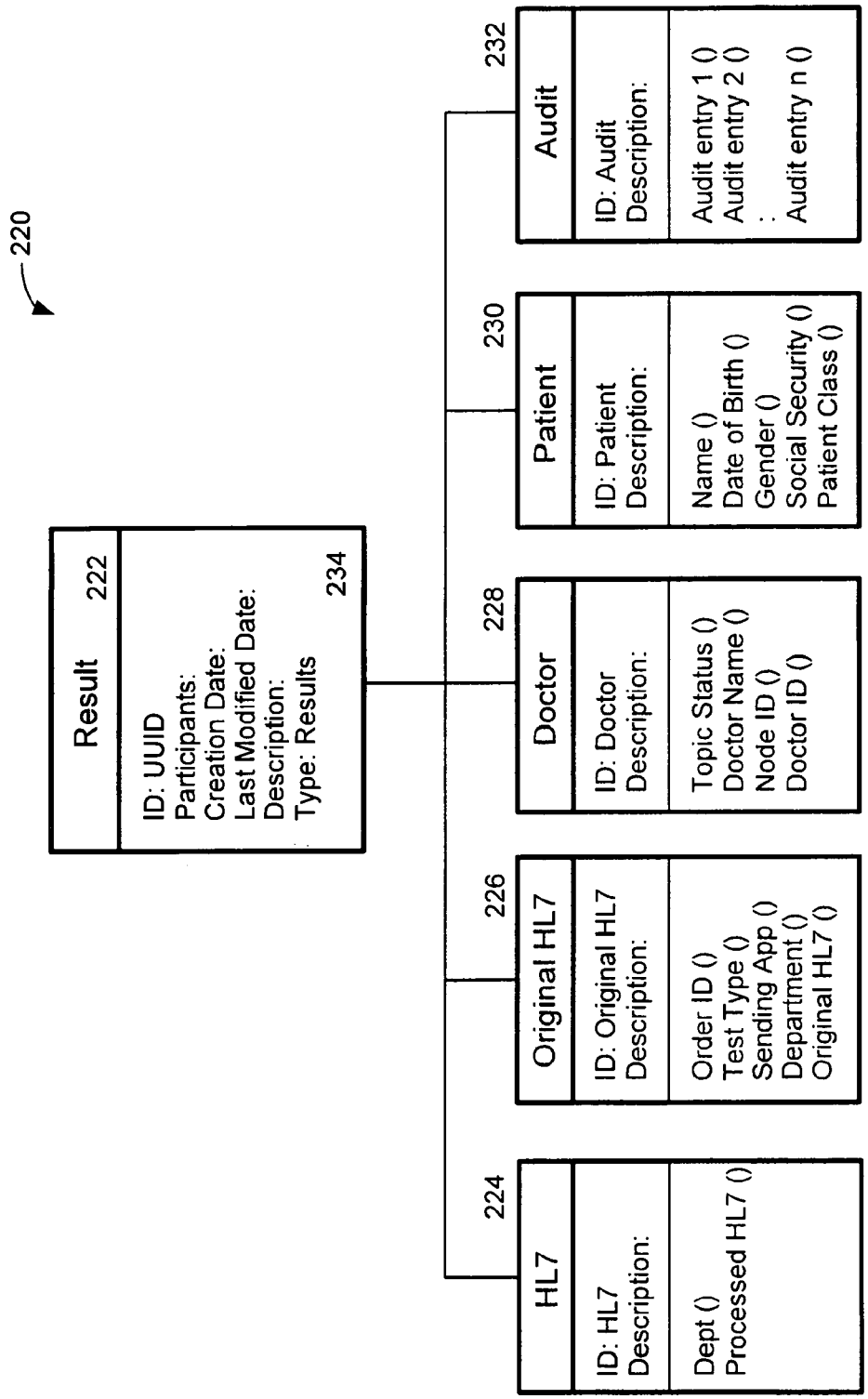
FIG. 8 is a depiction of a result topic object class according to the system of FIG. 1.

FIG. 8 illustrates an exemplary result topic object 220. A result topic object 220 may be used to exchange an HL7 message originating in one organization, such as a hospital, to another organization, such as a physician. The result topic object 220 includes the result class 222, result topic attributes 234 and result topic capsule objects 224, 226, 228, 230 and 232. The result topic attributes 234 include the ID, participants, creation date, last modified date, description and type, and contain the basic information necessary to distribute the result topic object 220 to participating nodes. The list of participants could include as few as two participants—the source participant (such as a hospital) and the destination participant (such as an ordering physician). The result topic object 220 may also be expanded to include other participants such as a consulting physician, or the patient, for example. The results topic object 220 may be replicated to the respective nodes of additional participants by simply adding each participant and their respective node ID to the result topic object attributes 234.

A result topic object 220 includes topic capsule object HL7 224 (HL7 capsule), topic capsule object original HL7 226 (original HL7 capsule), topic capsule object doctor 228 (doctor capsule), topic capsule object patient 230 (patient capsule) and topic capsule object audit 232 (audit capsule).

In the example of FIG. 8, (1) an HL7 capsule 224 contains the name of the originating department and the processed HL7 text string as rendered by the results agent. (2) An original HL7 capsule 226 contains the order ID, test type, sending application, originating department and also includes the original HL7 test string. (3) A doctor capsule 228 contains information about the ordering physician in the HL7 message, and includes name, node ID representing the physician, and the unique doctor ID used by the hospital to identify the physician in the HL7 messages. (4) A patient capsule 230 contains information regarding the patient in the HL7 message, and includes name, date of birth, gender, social security number, and patient class (e.g., inpatient, outpatient, etc.). An audit capsule 232 provides for the audit of events affecting the results topic object 220 (such as issued, transported, received, processed) and the HL7 ACK message returned by the receiving EMR or system.

Figure 9:
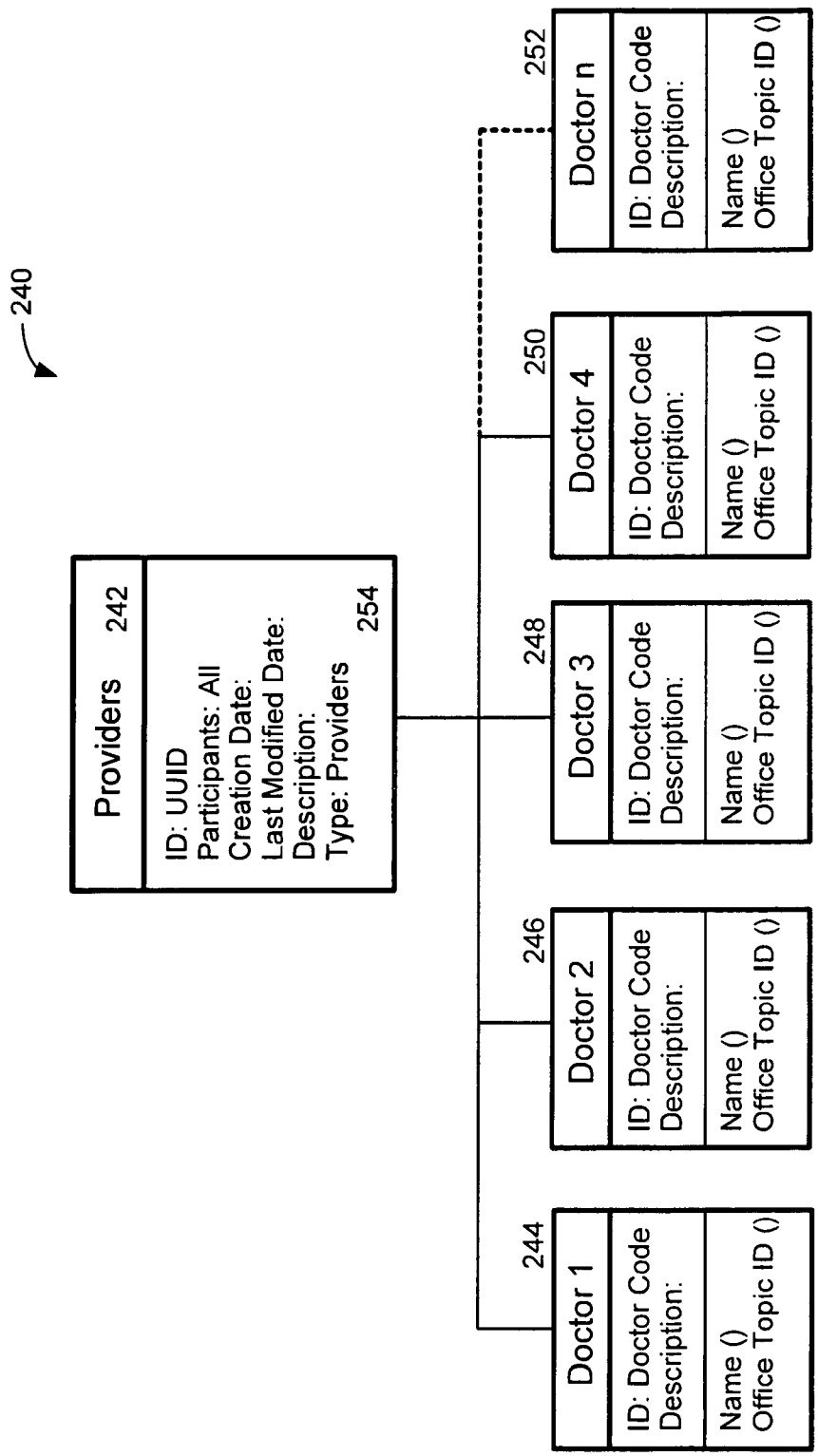
FIG. 9 is a depiction of a providers topic object class according to the system of FIG. 1.

FIG. 9 illustrates an exemplary provider topic object 240. A provider topic object 240 may be used to provide a directory of physicians configured to receive healthcare information. The provider topic object 240 includes the provider class 242, provider topic attributes 254 and provider topic capsule objects 244, 246, 248, 250 and 252 (provider capsules). The provider topic attributes 254 include the ID, participants, creation date, last modified date, description and type, and contain the basic information necessary to distribute the provider topic object 240 to participating nodes.

The provider topic object 240 includes an instance of a provider capsule object for each doctor that receives results through the distributed computing system grid. Specifically, each doctor capsule object 244, 246, 248, 250, 252 includes the name of the physician and the ID of the physician office topic object to provide additional information needed by the result application to process and distribute results.

Figure 10:
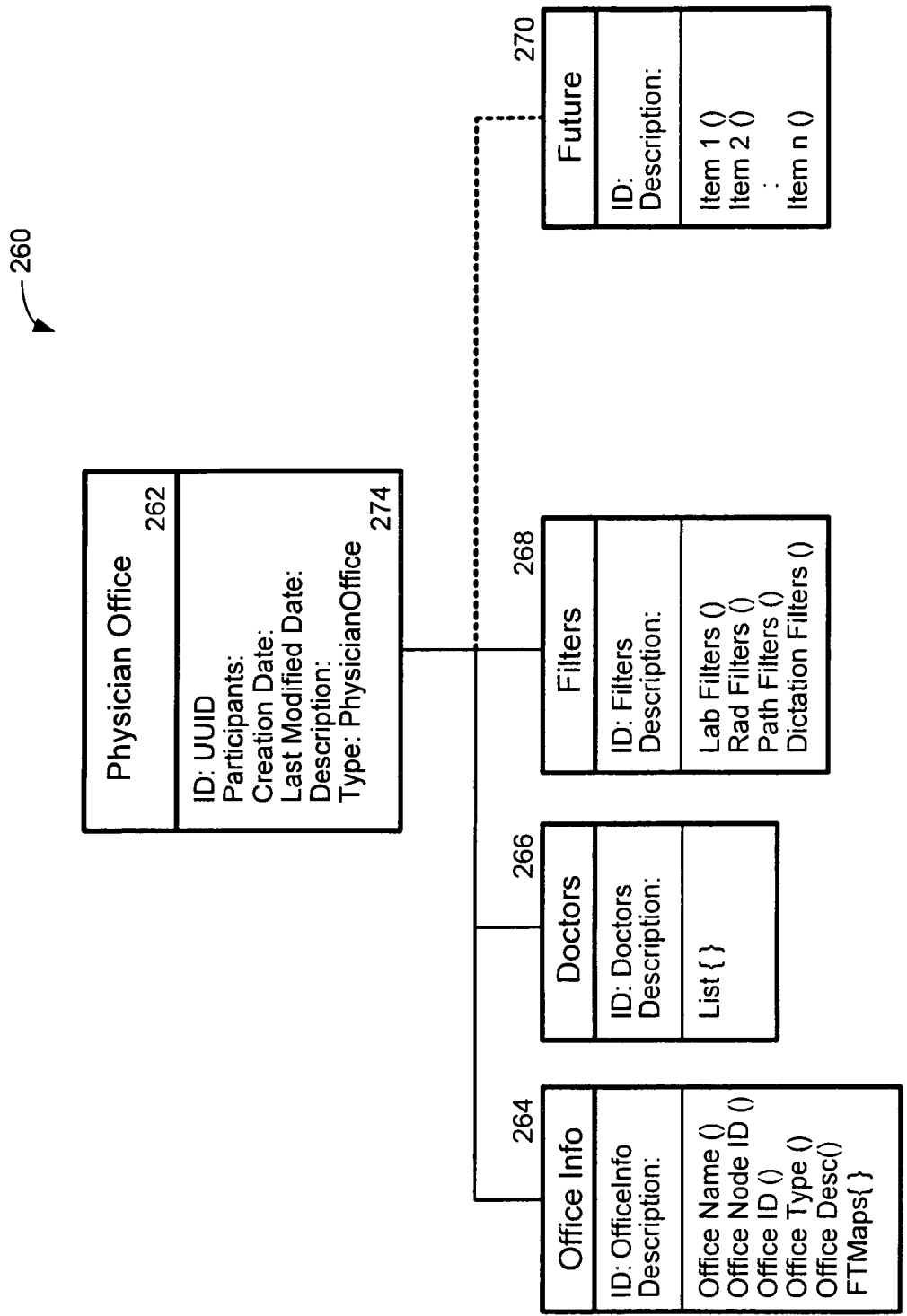
FIG. 10 is a depiction of a physician office topic object class according to the system of FIG. 1.

FIG. 10 illustrates an exemplary physician office topic object 260. A physician topic object 260 may be used to provide detail relative to the provider office and includes filtering, processing, transformation and delivery information. The physician topic object 260 includes the physician office class 262, physician office topic attributes 274 and physician office topic capsule objects 264, 266, 268, 270 (physician office capsules). The physician office topic attributes 274 include the ID, participants, creation date, last modified date, description and type, and contain the basic information necessary to distribute the provider topic object 240 to participating nodes.

The physician office topic object 260 includes specific physician office topic capsule objects that provide information relating to office information, doctors and filters. (1) The office info capsule object 264 provides general information relative to the office including name, node ID, office ID, office type, office description and special filter maps that instruct the results agent how to process HL7 messages for that particular office. (2) The doctors capsule object 266 includes a list of parties that may receive results, and includes physicians, physician assistants, nurses and other office personnel, and also including their respective IDs. (3) The filters capsule object 268 provides specific data used by the results agent to transform the HL7 into the proper format for the receiving EMR. Filters specific to result types, e.g., laboratory, radiology, pathology, and dictated reports, are also included. (4) The future capsule object 270 allows for expansion of the physician office topic object 260. As new agents and functions are added over time, the physician office topic object 260 may be expanded. Future capsule objects 270 may be created and added to the physician office topic object 260 to enable the configuration and execution of new agents 108 and programs on the node 104 in the particular office.

Payload

A payload structure facilitates the secure, asynchronous routing of information between nodes 104 via the rendezvous 102 for distribution of topic object 106 updates.

Figure 11:
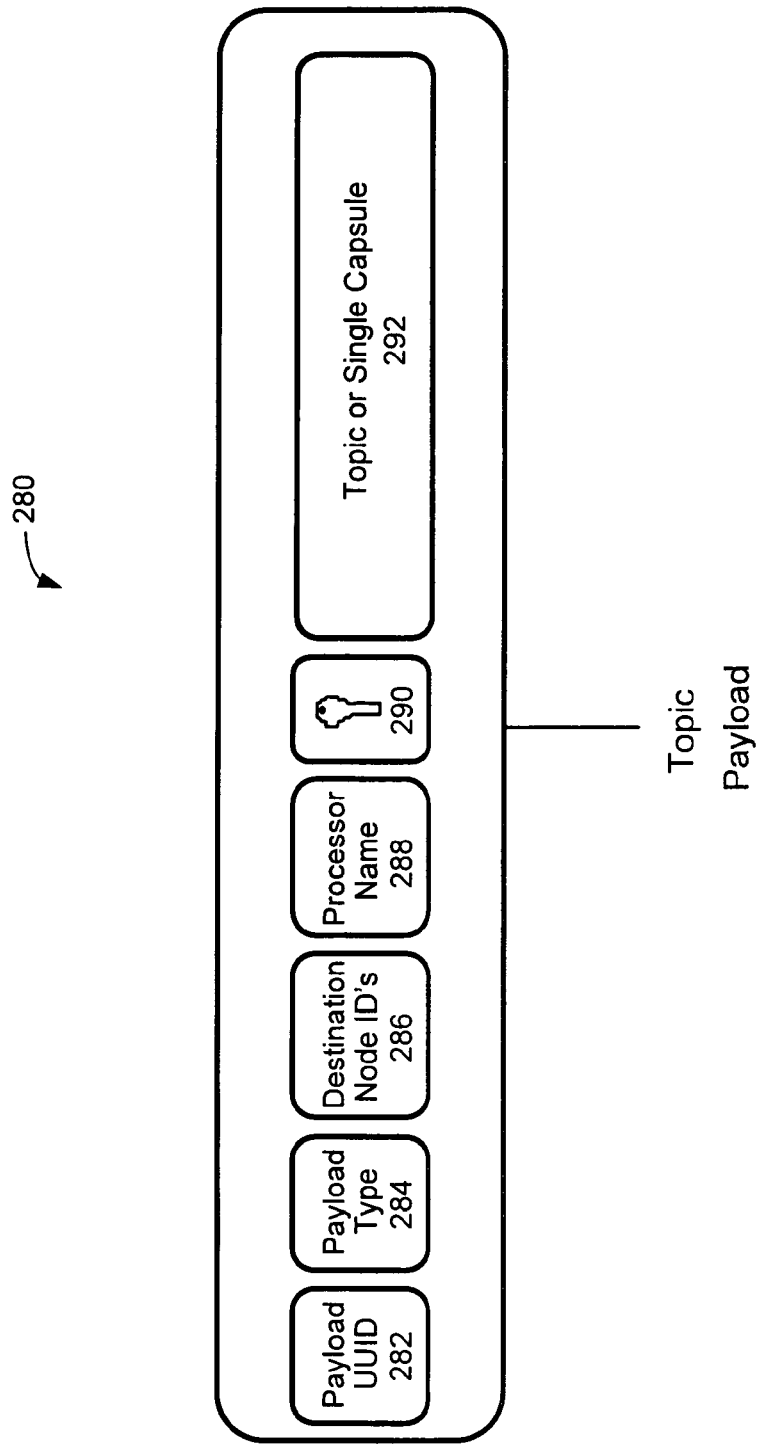
FIG. 11 is a depiction of a topic payload data stream according to the system of FIG. 1.

FIG. 11 illustrates an exemplary embodiment of the structure of a payload 280. A payload 280 is a serialized object and contains unique information that enables the rendezvous 102 to process, sort and queue the payload 280 for the designated destination node. As described above, the payload 280 is created by the payload generator 154 at a particular node 104.

A payload 280 includes a unique payload ID 282, the payload type 284, a list of destination nodes 286, the processor ID 288, the payload key 290 and the topic data 292. The payload ID is unique to the payload 280 and is used by the rendezvous 102 and the nodes 104 to manage and sort the payloads 280. The payload type 284 is typically a topic payload or a single capsule payload. The list of destination nodes 286 includes the nodes that participate in or are related to the information or data included in the payload 280. The processor ID 288 provides the name of the agent that processes the payload. The payload key 290 is a unique, symmetric key used to encrypt and decrypt the payload 280. The topic data 292 (or capsule data) is the data that is included in the payload 280.

A payload 280 may be used to provide new data via a new topic object, or a data update via a topic object update, for example. One example would be the addition of new nodes or participants to an existing topic.

A payload 280 may also consist merely of single capsules in the topic data 292 portion.

Figure 12:
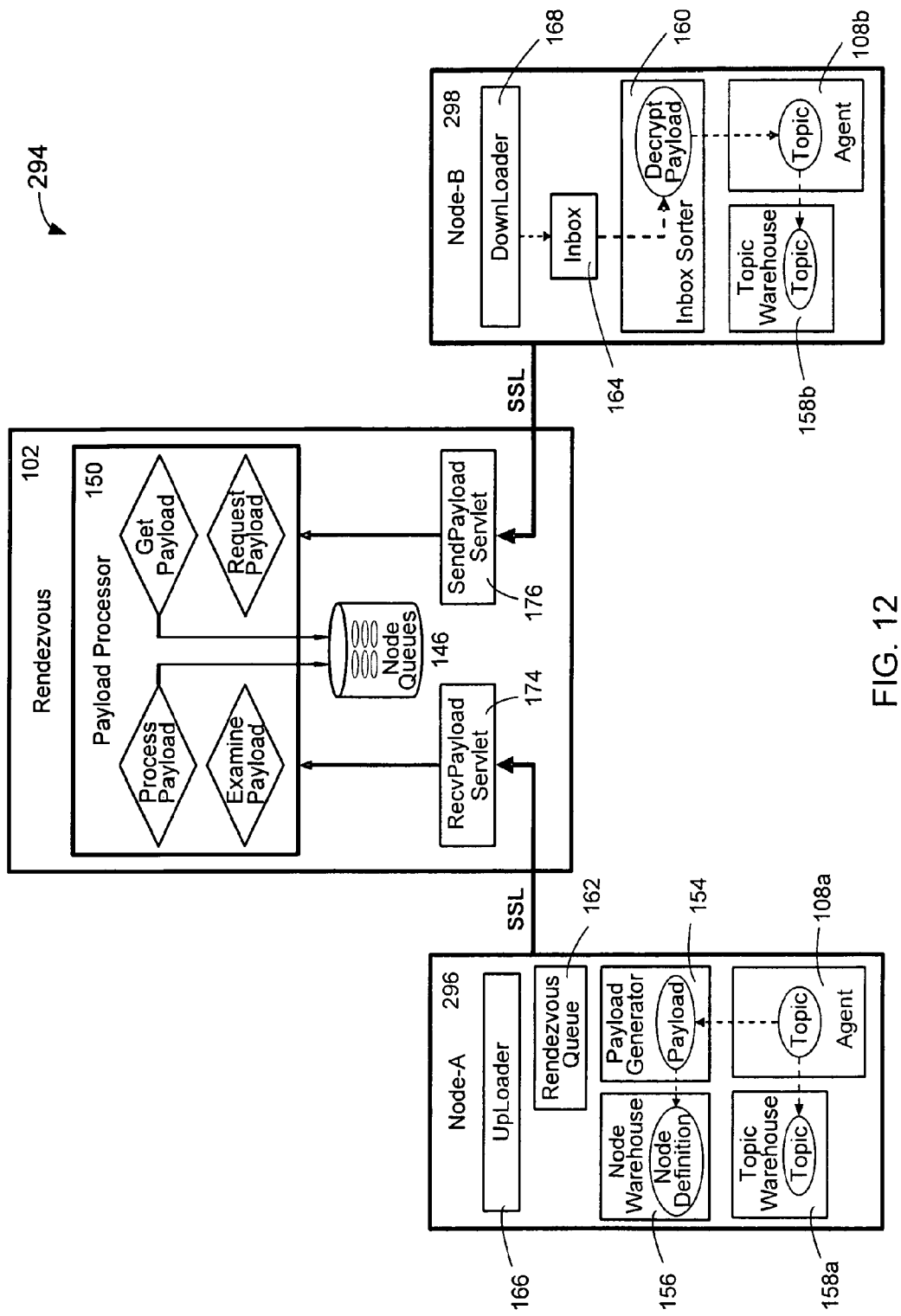
FIG. 12 is a block diagram of an exemplary system for payload exchange between two nodes according to the system of FIG. 1.

FIG. 12 illustrates an exemplary embodiment of a system 294 enabling a payload exchange between two nodes. It should be noted that node-A 296 and node-B 298 have similar functionality, though in the interest of clarity only those components necessary for creating and sending a payload are shown in node-A 296 while only those components necessary for receiving and processing the payload are shown in node-B 298. The roles could just as easily be reversed allowing node-B 298 to create and send a payload to node-A 296.

An agent 108a at node-A 296 desires to send a payload to node-B 298. The agent saves a copy of the topic object 106 in the local topic warehouse 158a, and then passes the topic object 106 to the payload generator 154.

The payload generator 154 determines the list of participating node IDs from the topic object attributes. The node definition for each node participating in the topic object is acquired from the node warehouse 156 for use in encrypting the payload 280. The topic object 106 is then encrypted and streamed into a new payload 280. Attributes are added to the payload 208 that enable the rendezvous 102 and destination nodes (node-B 298 in this instance) to receive and process the payload 208. The newly created payload 280 is then saved in the rendezvous queue 162.

The uploader 166 monitors the contents of the rendezvous queue 162 for new payloads on a regular basis. The monitoring period is configurable by the node (node-A 296 in this instance). Upon discovering a new payload 280, the uploader establishes a secure session with the receive payload servlet 174 at the rendezvous 102 and streams the encrypted payload 280 to the rendezvous 102.

Upon receiving the payload 280 at the receive payload servlet 174, an acknowledgment of payload receipt is returned to the uploader 166. Node-A 296 deletes the payload from its rendezvous queue 162 upon receiving the acknowledgment.

At the rendezvous 102, the receive payload servlet 174 passes the payload to the rendezvous payload processor 150 for processing. The payload processor examines the payload attributes to determine the participating nodes that are to receive a copy of the payload. A copy of the payload 280 is then placed into the node queue 146 corresponding to each destination node (node-B 298 in this instance).

At the receiving node (node-B 298 in this instance), a downloader 168 routinely connects via secure session to the send payload servlet 176 at the rendezvous 102 and requests payloads 280 from its corresponding node queue 146. The send payload servlet 176 forwards the request to the payload processor 150. The payload processor 150 returns the contents of the node queue 146 corresponding to node-B 298. The node queue contents include the new payload sent from node-A 296. The node queue contents are streamed to the downloader 168 at node-B 298 over a secure session.

Upon receiving the encrypted payload from the rendezvous 102, the downloader 168 saves the encrypted payload into the inbox 164 at node-B 298. An inbox sorter 160 reads the encrypted payload from the inbox 164 and decrypts the payload 280. The topic attributes of the payload 280 are examined for determination of the agent 108b to be evoked for topic object processing. The topic object 106 is then passed to the agent 10b'.

The local agent 108b processes the topic object 106 and takes action based programmed rules within the agent 108b. For the circumstance where the topic object 106 is new, it can be added to the local topic warehouse 158b. For the circumstance where the payload contains a capsule object for an existing topic object 106, the existing topic object 106 within the topic warehouse may be located and the capsule object may be added to the existing topic object 106. Thus, a node may provide new information or updated information to other nodes.

The payloads 280 are typically encrypted via combining elements of asymmetric and symmetric encryption mechanisms with SSL. Of course, those with skill in the art will understand that other encryption methodologies may be adapted for use in the system.

Figure 13:
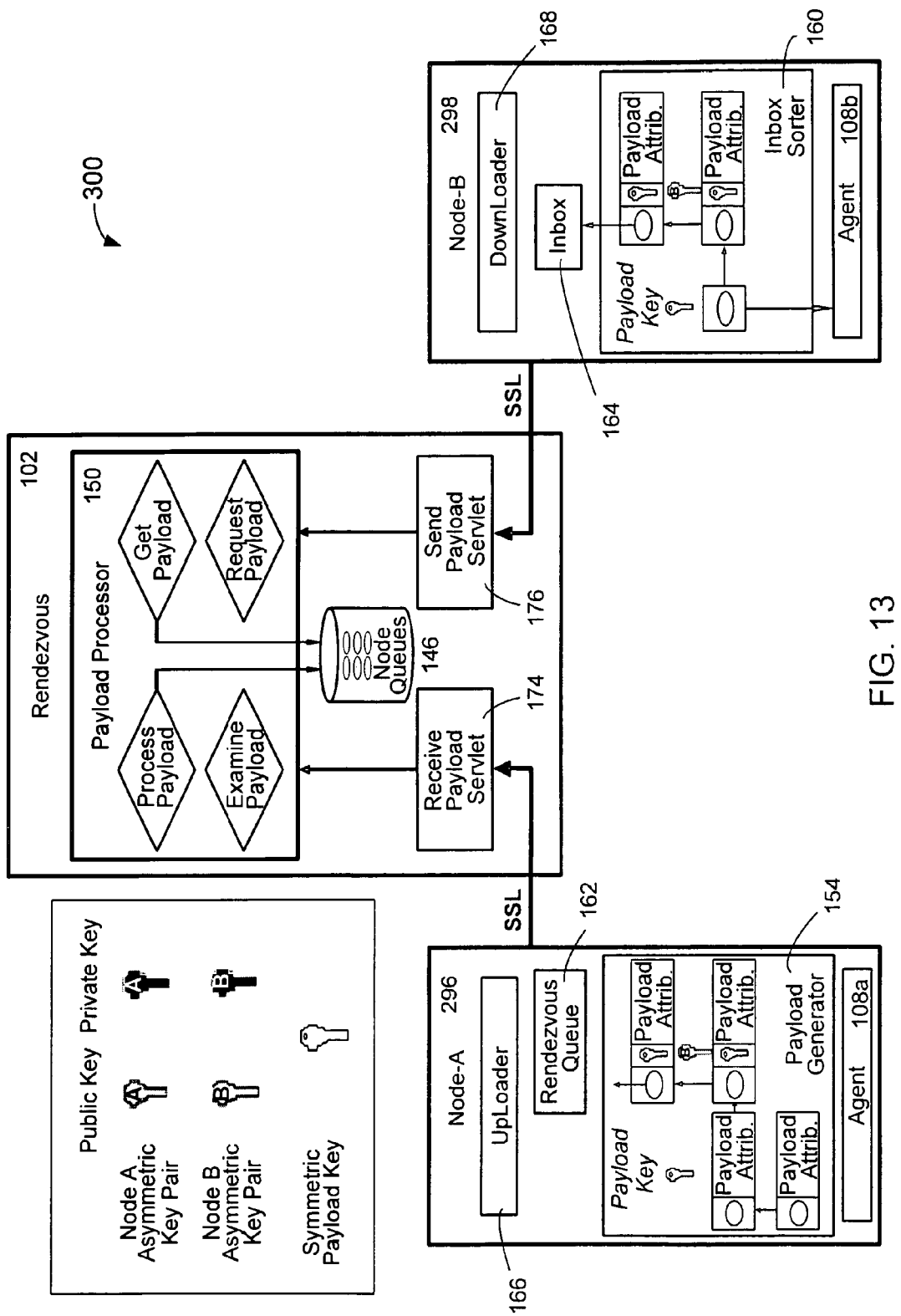
FIG. 13 is a block diagram of an exemplary system for payload encryption and distribution according to the system of FIG. 1.

FIG. 13 illustrates an exemplary embodiment of a system 300 for payload encryption and distribution via a rendezvous. It should be noted that node-A 296 and node-B 298 have similar functionality, though in the interest of clarity only those components necessary for creating and encrypting a payload are shown in node-A 296 while only those components necessary for receiving and decrypting the payload are shown in node-B 298. The roles could just as easily be reversed allowing node-B 298 to create and encrypt a payload for node-A 296.

Before describing payload encryption, a brief description of node and rendezvous setup is necessary. All nodes generate a unique asymmetric key pair upon node creation. The private key is stored by the node. The public key is distributed to all nodes via the node's definition topic and is stored in their respective node warehouse 156. Nodes may thus use the public and private keys to encrypt and decrypt data according to the public key infrastructures (PKI) as it relates to encryption and digital signatures.

During creation of a payload, the payload generator 154 generates, for example, a unique 2048-bit AES symmetric key denoted as the payload key. This key is used to encrypt the topic object 106 data in the payload. The payload is created to distribute the topic object to participating nodes and is secured via the following:

(1) Node-A 296 creates a payload including attributes for distributing the payload to a list of participating nodes.
(2) Node-A 296 generates a payload key and utilizes the payload key to encrypt the topic object data.
(3) The payload generator retrieves the public key for each participating node from the node warehouse 156. For each participating node, the payload generator encrypts a copy of the payload key with that node's public key and adds it to an array of encrypted keys.
(4) The payload attributes, encrypted topic object data, and array of encrypted payload keys are streamed into the payload and saved in the rendezvous queue 162 at node-A 296.
(5) The uploader 166 at node-A 296 establishes and maintains a one-way secure session with the rendezvous 102. The payload is retrieved from the rendezvous queue 162 and streamed over the secure session to the receive payload servlet 174 at the rendezvous 102.
(6) The receive payload servlet 174 passes the payload to the payload processor 150 at the rendezvous 102.
(7) The payload processor 150 examines the payload attributes for the IDs of the participating nodes. For each participating node, the payload processor 150 saves a copy of the payload into the node queue corresponding to that node destination.
(8) The downloader 168 at node-B 298 regularly connects to the send payload servlet 176 to request payloads from its corresponding node queue 146 at the rendezvous 102. The send payload servlet 176 passes the request to the payload processor 150, and the payload processor 150 retrieves the payload from the node queue 146 corresponding to node-B 298. The payloads retrieved from the node queue 146 are passed to the send payload servlet 176. The payloads are then streamed to the downloader 168 at node-B 298 via a secure session, such as HTTP/S.
(9) The downloader 168 saves the payloads into the inbox 164 at node-B 298.

Upon receiving the payload at node-B 298, the inbox sorter 160 reads the payload from the inbox 164, utilizes the private key of node-B 298 to decrypt the payload key, and uses the payload key to decrypt the topic object 106. Once decrypted, the inbox sorter 160 passes the topic object to the appropriate agent 108 as denoted in the topic object attributes.

Data is encrypted from the time it is sent by the sending agent 108 until it is received by any participating agents 108'. Furthermore, the payloads can be decrypted only by the participating nodes 104.

Software Agents

A platform is provided for autonomous software agents to execute on each node. Topic objects 106 are used by the agents 108 for managing and persisting information as they collaborate on particular tasks. (1) Agents can create topic objects 106 and distribute them to participating nodes 104 for collaboration. The participant nodes are defined via the topic object attributes and the topic object is then forwarded to the participants via the rendezvous 102. (2) Agents may control the creation and definition of a topic object 106 as well as determining how the topic object 106 is used, and this control requires only the topic object capsule and the capsule structure. (3) Data may be read, written, removed and modified within the topic object capsules. (4) Topic objects 106 may be distributed, updated and deleted. (5) Agents may be called or evoked whenever a payload containing the agent ID is received at a node.

A results agent may be used for interfacing to EMR systems and for placing formatted HL7 data into the EMR inbox folder. Further, the results agent may monitor for HL7 acknowledgment from the EMR for return to the source as part of an audit.

Results Agent

Many healthcare information systems, including EMR's, use the HL7 standard for data exchange. The HL7 standard defines a message structure for common medical transactions such as ordering tests and receiving results.

Figure 14:
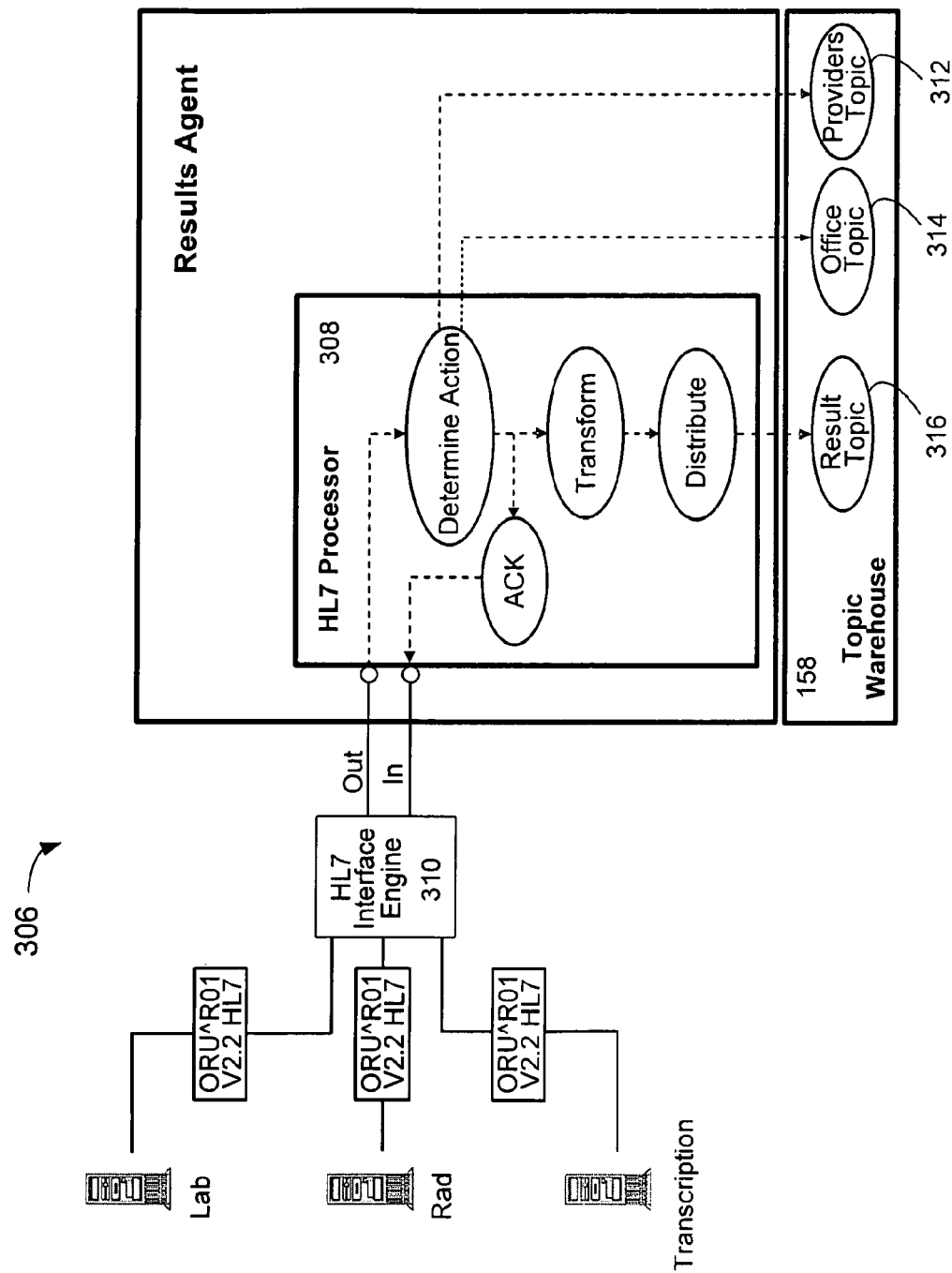
FIG. 14 is a block diagram of an exemplary results agent in a hospital setting according to the system of FIG. 1.
Figure 15:
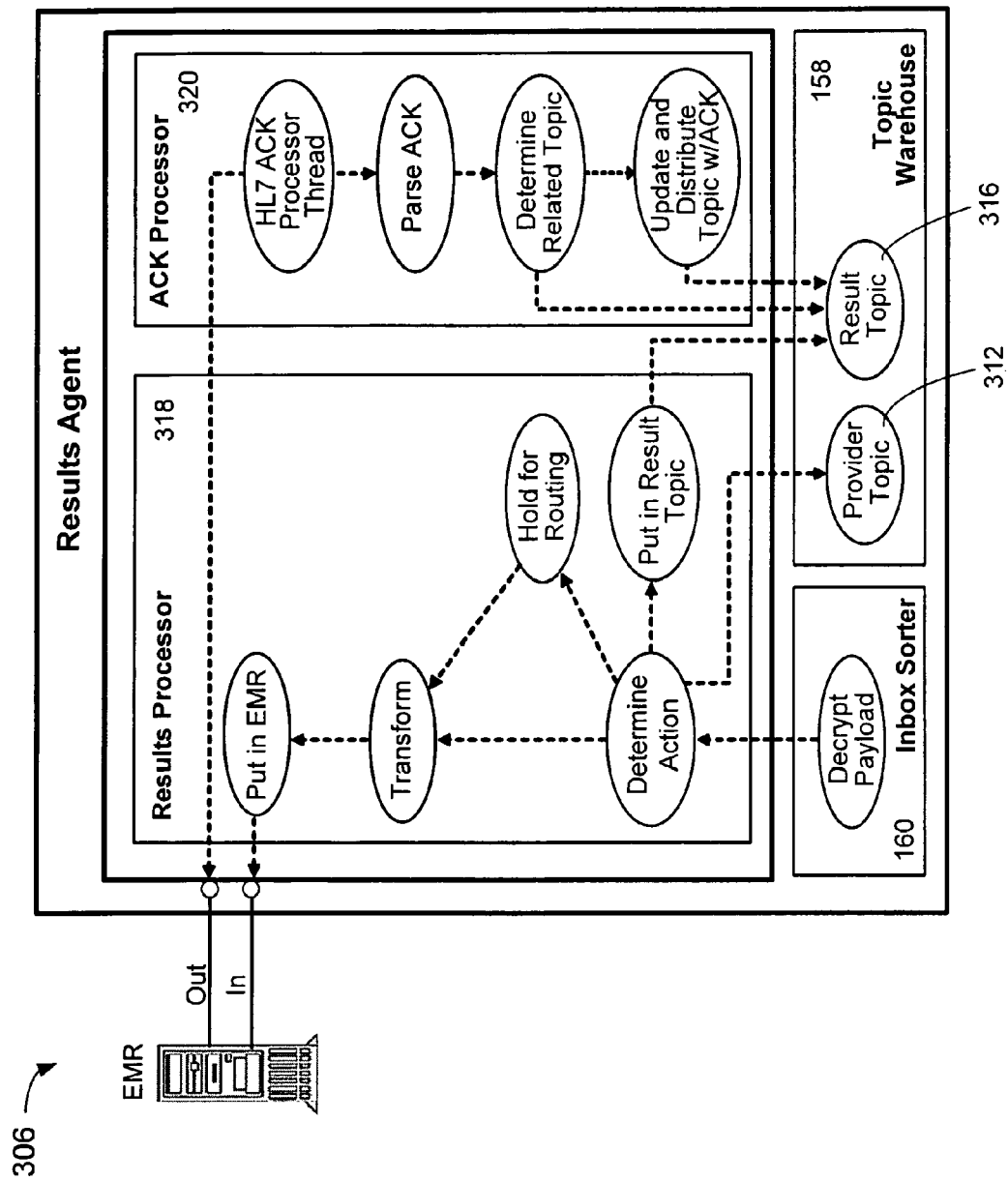
FIG. 15 is a block diagram of an exemplary results agent in an EMR setting according to the system of FIG. 1.

FIG. 14 illustrates an exemplary embodiment of a results agent 306 in a hospital setting while FIG. 15 illustrates an exemplary embodiment of a results agent 306 in an EMR setting.

The results agent provides mechanisms to capture, parse, analyze, transform, distribute, and insert HL7 messages between remotely located healthcare information systems like EMRs and hospital information systems (HIS). Since the results agent 306 is a distributed application, it is best understood from the perspective the functions that execute at each node 104. The results agent 306 includes mechanisms to (1) capture and transform, (2) receive and insert, and (3) audit the exchange. FIG. 13 provides the perspective of mechanisms executing at a hospital node, while FIG. 14 provides the perspective of mechanisms executing at an EMR such as at a physician office node.

FIG. 14 depicts a hospital results agent 306 that includes an HL7 processor 308. The HL7 processor 308 interfaces to the local application environment at the node 104. The HL7 processor 308 is connected to an HL7 interface engine 310 on a configurable TCP port and monitors for HL7 messages received over the interface engine's outbound interface.

Upon receiving an HL7 message, the HL7 processor 308 parses the message via converting the HL7 text string into objects that are directly usable by the HL7 processor 308. The HL7 processor 308 analyzes the objects and determines necessary actions such as discard, processing, and/or filtering the received messages.

A provider topic object 312 provides an index allowing the HL7 processor 308 to obtain a list of physicians that may receive the HL7 information. This list of physicians is an example of nodes that participate in or have a need-to-know regarding a particular topic object 106 (the provider topic object in this instance). The physician IDs in the received HL7 message are compared to the index of physicians and their associated IDs within the provider topic object. If a match occurs, the HL7 message is further processed. If there is no match, then the HL7 message is discarded.

Upon a physician ID matching a physician in the provider topic object index, the HL7 processor opens the physician office topic object 314 for that physician's office and obtains additional filtering and processing rules.

The HL7 processor creates an HL7 ACK for return to the HL7 interface engine. After acknowledging the received message, the HL7 processor transforms the HL7 based on configuration parameters and preferences identified in the physician office topic object and specific configuration files. Configuration parameters include: (1) department identifiers indicating which department messages to process, (2) result status filters to determine which HL7 messages of a particular status type are to be sent, (3) patient type filters specifying which test results are sent based on the patient type in the HL7, (4) HL7 department strings providing information that can be added to the HL7 making it suitable for sending, such as adding a lab director name or other data not included in the original message, and (5) processing instructions for the HL7 processor to prevent duplications.

The HL7 processor creates an instance of the results topic object 316 and adds the hospital and interested physicians as participants in the results topic object 316. The HL7 text is streamed into the results topic object 309 and then the results topic object 316 is saved to the local topic warehouse 158. The HL7 processor then distributes the new results topic object 316 to the destination nodes by passing the results topic object 316 to the payload generator 154 as previously discussed.

The node then delivers the payload to the destination nodes via the rendezvous 102.

FIG. 15 depicts a results agent 306, in an EMR setting, that includes a results processor 318 and an ACK processor 320. The results agent 306 typically operates in a physician office where the EMR is physically located. The results processor 318 places HL7 messages into the EMR's inbound interface. The ACK processor receives HL7 ACK message from the EMRs outbound interface.

The process is initiated when a new payload is placed into the inbox 164 and processed by the inbox sorter 164. The inbox sorter 164 decrypts the payload, extracts the results topic object 316 and passes the results topic object 316 to the agent 108 identified in the topic object attribute.

The results agent 306 analyzes the results topic object 316 to determine the topic object type. The topic warehouse 158 is accessed to locate a provider topic object 312. Parameters and preferences are retrieved from the provider topic object 312 and are applied by the results agent 306 to transform and/or filter the newly received HL7 message.

The results agent 306 scans the topic warehouse 158 for a replica of the newly received results topic object 316, utilizing the topic object's unique ID. If a replica of the results topic object 316 is found, the results agent 306 opens the results topic object 316 and adds the newly received data to the results topic object 316 located in the topic warehouse 158. If no replica of the results topic object 316 exists, then the results agent 306 adds the new results topic object 316 to the topic warehouse 158.

Upon saving the results topic object 316 in the topic warehouse 158, the agent 108 determines whether to continue processing the received HL7, or hold the HL7 to acquire additional routing information before continuing. If an HL7 message is held for routing, the results agent 306 provides several JSP applications that enable examination and modification of the HL7 message via a web browser.

A common examination and/or modification example is an outpatient test result that has been delivered to the physician office. An outpatient test generally does not require an ordering physician to be included. Since many hospitals require an ordering physician to be identified to fulfill the order, the hospital often inserts a generic physician identifier as the ordering physician (often the top physician in the group). In order to route the result to the appropriate physician at the physician's office, a nurse generally determines the correct provider (physician, physician assistant, or nurse) to route the HL7 result message.

The results agent 306 enables office staff to view all HL7 results from a browser-based work list. The work list typically contains a column with a pull down list of providers in the office. A nurse, or other office personnel, selects the provider that should receive the HL7 from the pull down list. Once selected, the results agent 306 acquires the newly selected provider and transforms the ordering physician in the HL7 from the original generic physician to the newly selected provider.

The results processor 318 utilizes the parameters found in the configuration topic object to transform the HL7 message. The transformation could include filtering specific elements of the HL7 message, adding or transforming elements, or other modifications as defined in the node's configuration objects and topic objects.

After completing all necessary transforms, the results processor 318 places the processed HL7 message into the EMR's inbound interface. The EMR inbound interface is typically a folder located on the EMR server, thus the results agent 306 copies the HL7 text string to the folder with the required file extension dictated by EMR requirements.

The EMR then processes the HL7 text string, matching the patient and provider found in the HL7 message with the patients and providers found in the EMR database. For patients, the EMR typically uses a reconciliation process to examines the patient's name, date of birth, gender, social security number or other specific elements and compare them against a list of patients in the database. Upon detecting a match, the EMR can, for example, associate the patient result in the HL7 message with a patient's record in the EMR. Providers likewise, are typically matched using the physician ID code. Of course, those of skill in the art will readily understand that any number of patient parameters and information could be used for matching patients with a list of patients in a database. The same holds for matching physicians with a physician list.

If a provider and/or patient's identity cannot be resolved, the EMR can, for example, queue the HL7 into a reconciler to enable access for manually matching the provider or patient to one in the EMR.

If the EMR uses an HL7 interface, it typically deposits an HL7 ACK message in the outbound interface on the EMR (often a unique folder on the EMR server).

The ACK processor 320 retrieves the HL7 ACK from the EMR's HL7 outbound interface. Upon finding a new message, the ACK processor reads the HL7 text, parses the text into objects and determines the result with which the HL7 ACK is associated.

The results agent 306 searches the topic warehouse 158 for result topic objects 316 that match the HL7 ACK. Upon finding a matching result topic object 316, the result topic object 316 is opened and the audit capsule object within the result topic object 316 is updated with the new HL7 ACK. The HL7 ACK is discarded if no matching result topic object 316 is found.

After the result topic object 316 is updated on the physician office node by the ACK processor 320, the audit capsule object can be distributed back to the source node (the hospital in this instance) to be added to the replica of the result topic object stored on the hospital node, thus providing an audit trail.

The HL7 processor 308, the results processor 318, and the ACK processor comprise the major components of a results agent 306.

In one embodiment, the results agent 306 extends a hospital's HL7 interface environment to remote locations. The results agent 306 captures, analyzes, transforms and distributes HL7 messages to other agents, processing them to suit the local needs of users and/or applications.

The results agent 306 uses an HL7 parser to convert the incoming HL7 text into Java objects that are manipulated by the agent 108.

In another embodiment, the Java objects are converted into HL7 text for delivery to remote HL7 application interfaces and folders.

Agents 108 analyze the message and take action based on preferences, rules and requirements. The HL7 is processed to create a message suitable for distribution, which includes filtering, mapping, or adding additional information to the message.

For example, distribution of HL7 clinical results and reports is performed by reading the segments of the HL7 message that identify the ordering physician that is to receive the result. The agent 108 uses the information in the physician office topic object to get rules for handling the HL7. The agent 108 automatically processes the information and securely distribute it to another agent 108 installed on a node 104 in a physician's office connected to that physician's EMR.

Remote Management

Figure 16:
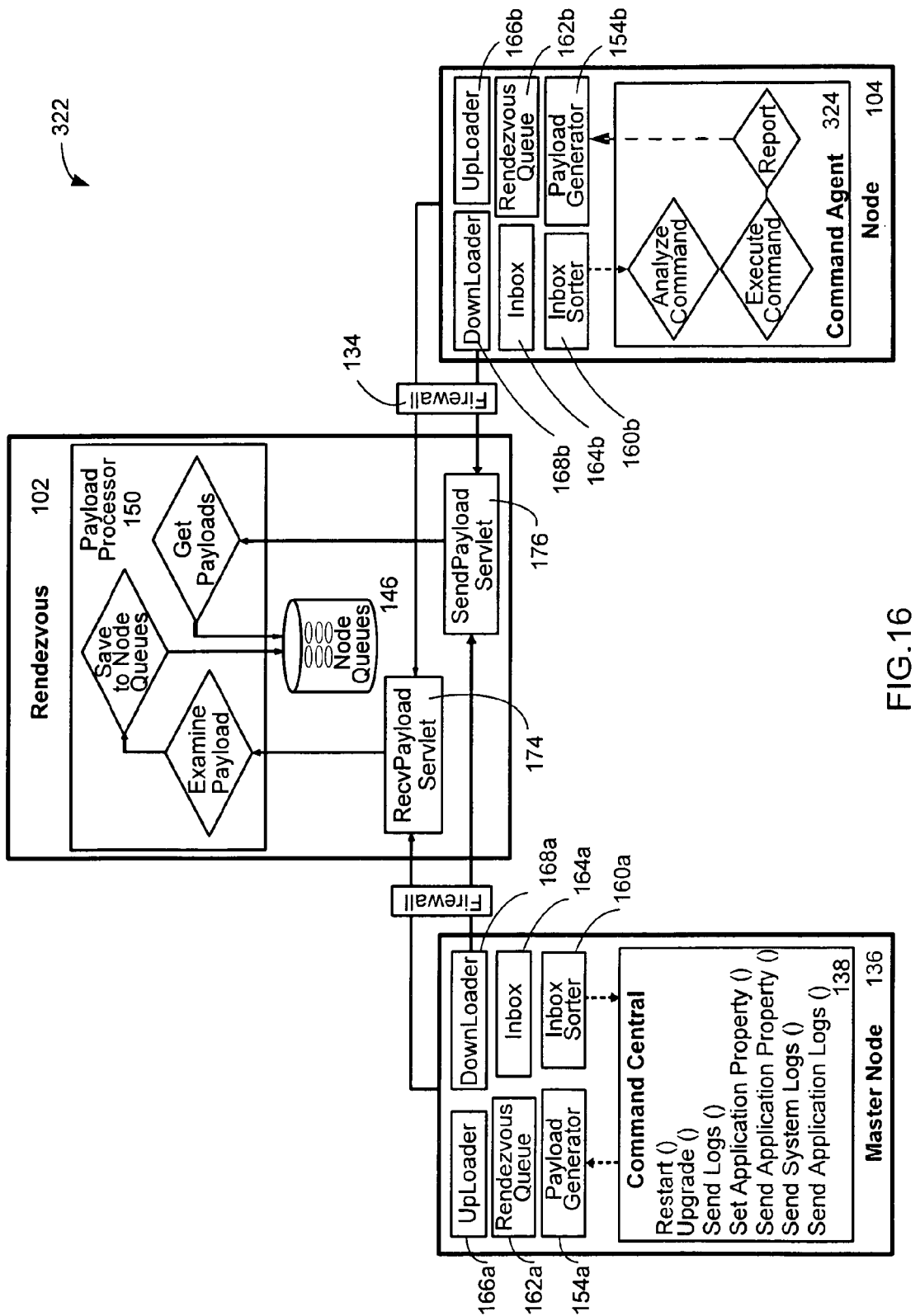
FIG. 16 is a block diagram of an exemplary system for remote management of nodes and agents according to the system of FIG. 1.

FIG. 16 illustrates an exemplary embodiment for remote management 322 of nodes and agents in the system. Healthcare applications are often installed in a wide variety of settings and including locations where little or no technical expertise is available. Thus, the source of commands to nodes 104 and agents 108 should be identified as a trusted source. A system administrator has the authorization to manage the nodes 104 and agents 108.

In one embodiment, a master node 136 (command central) enables system administrators to securely issue commands to a node 104 from a trusted source, and also to receive responses providing status and/or requested information such as log files. The master node 136 also provides a launching point to generate, deploy and enable nodes and agents.

Upon initial creation of a node 104, the node ID of the master node 136 is assigned. Initially, nodes will accept and process only commands from the master node 136. A command agent 324 operates at each node 104. The command agent 324 at each node 104 receives, executes and reports the status of the command payloads issued from the assigned master node 136.

A command central 138 process operates at the master node 136 and provides functionality allowing system administrators to manage nodes 104 and agents 108 from a central location. The command central 138 process includes (1) applications that provide the system administrator's user interface, (2) a library of commands that can be executed by the remote command agents 324 and (3) functionality to receive responses from the command agents (through a command topic object 330 discussed below) and present it to the system administrator. The library of commands executable by the remote command agents 324 typically include, as non-limiting examples, the capability to (a) restart the node, (b) upgrade the software, (c) set an application property, (d) send logs to the system administrator, (e) send an application property, (f) send system log files and (g) send application log files.

In one embodiment, the system administrator accesses command central 138 from the master node 136. The master node 136 provides username and password protection, requiring secure login. Upon logging in, the system administrator has capability to select commands, input parameters and send the command to a selected node 104.

Upon issuing a command, command central 138 creates an instance of a command topic object 330. The command and associated parameters are streamed into the command topic object 330. Command central then passes the command topic object 330 to the payload generator 154a at the master node 136. The payload generator 154a creates a command payload and places the command payload in the rendezvous queue 162a on the master node 136. The uploader 166a then connects to the receive payload servlet 174 at the rendezvous 102. The receive payload servlet 174 passes the command payload to the payload processor 150. After processing, the payload processor 150 places the command payload in the node queue corresponding to the node 104 to receive the command.

The downloader 168b at the receiving node 104 connects to the send payload servlet 176 at the rendezvous 102 to download the command payload. The command payload is placed in the inbox 164b at the receiving node 104. The inbox sorter 160b retrieves the command payload from the inbox 164b, extracts the command topic object 330 and then passes the command topic object 330 to the command agent 324.

The command agent 324 analyzes and executes the command as determined the processing logic of the command agent 324. Upon executing the command, a response is generated and added as a capsule object to the command topic object 330. The command topic object 330 is passed to the payload generator 154 at the node 104. The payload generator places the command topic object 330 into a payload and routes it back to the master node 136 as discussed previously.

The uploader 166b, the rendezvous queue 162b, and the payload generator 154b at node 104 operate in similar fashion for sending messages to the master node 136. Similarly, the downloader 168a, the inbox 164a, and the inbox sorter 160a operate as expected for receiving messages at the master node 136.

The master node 136 receives the payload from the receiving node 104 and presents the response to the system administrator via a browser-based view.

Figure 17:
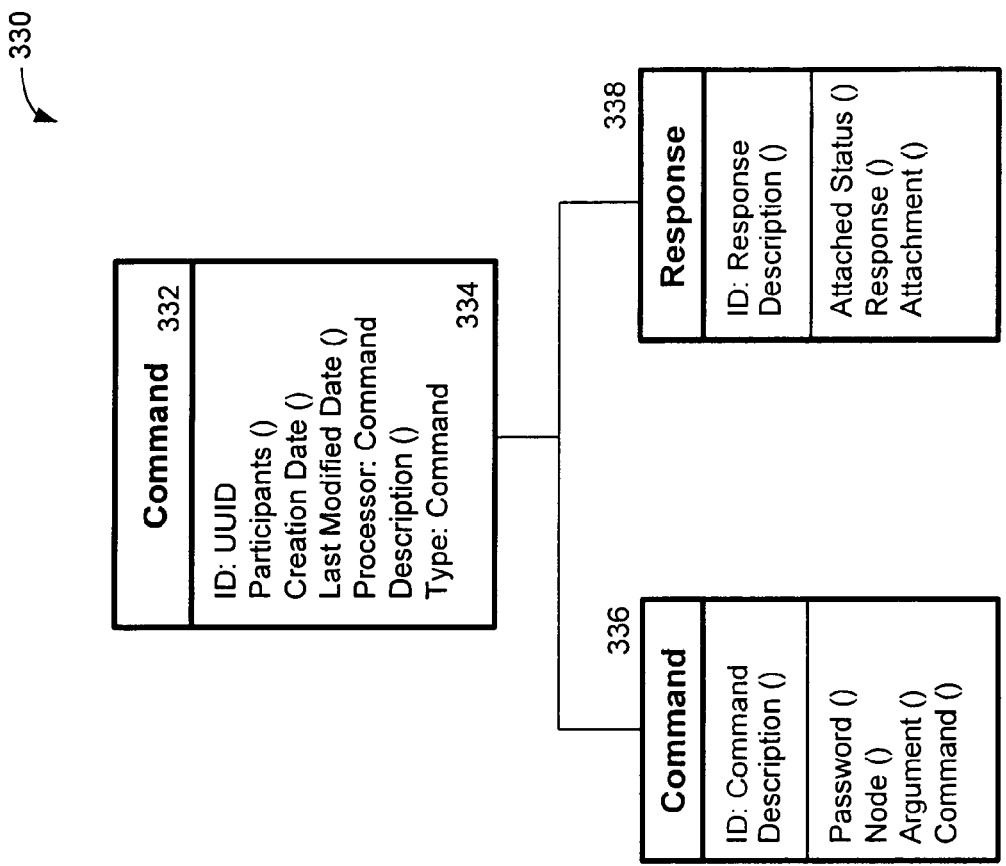
FIG. 17 is a depiction of a command topic object class according to the system of FIG. 1.

FIG. 17 illustrates an exemplary embodiment for a command topic object 330. The command topic object 330 includes the command class 332, command topic attributes 334, command capsule objects 336 and response capsule objects 338. The command class topic attributes include the topic type "Command" and the name of the processor "Command."

The command capsule object 336 provides information relative to the issued command, and includes the command, command arguments, the node ID to which the command is issued, and a password, for example. In one embodiment, the password is typically used by the node to authenticate the command upon receipt. A command is executed at a node 104 if the command capsule object contains the correct password and if the password originated from its assigned master node. Of course, those of skill in the art will note that authentication is not limited to a password, and other authentication methods can be used.

The response capsule object 338 provides functionality for returning responses from the command agent 324 at the node 104. The response capsule object 338 includes status, response detail and attachments such as log files.

In one embodiment, a command topic object 330 is created and saved to a topic warehouse 158 (not shown) at the master node 136. The command central 138 streams the command topic object 330 into a payload generator 154' which then generates a command payload, encrypts the payload, and places the payload into the rendezvous queue 162' at the master node 136.

As described previously, the uploader 166 monitors the rendezvous queue 162 for payloads, and upon discovering a new command payload, establishes a secure session with the receive payload servlet 174 and streams the command payload to the rendezvous 102. The payload processor 150 then processes the command payload and places it into the node queue 146 corresponding to the node 104 to receive the command.

As discussed above, the downloader 168 establishes a secure session with the rendezvous 102 and downloads the contents of its node queue 146. The send payload servlet 176 at the rendezvous 102 streams the command payload to the downloader 168 and the command payload is placed in the inbox 164 at the node 104.

The inbox sorter 160 retrieves the command payload from the inbox 164, extracts the command payload containing the command topic object, decrypts the command payload and passes the extracted command topic object to the agent 108 identified via the command topic attributes—the command processor.

A command processor receives the command topic object and extracts the contents of the command capsule object 336, which includes the issued command and attributes. The password in the command capsule object 336 is compared with the node's assigned password. If the passwords match, and the command originated from the node's assigned master node, the command processor continues processing the command. If the passwords do not match, or if the command originated from a node other than the node's assigned master node, then the command topic object 336 is discarded.

Upon verifying authenticity of the command, the command processor executes the command. The command typically includes such functionality as executing local processes to set an application parameter or collect information such as system log files, for example.

Upon executing the command, the command processor creates a response and streams the response into the response capsule object 338. A payload containing the response capsule object is created, encrypted and then returned to the master node 136 as described earlier.

Command central 138 receives the payload, decrypts the payload and analyzes the contents. The topic warehouse 158 is searched for a command topic object ID matching the ID of the topic object in the payload. Upon locating a matching command topic object 330, the instance of the command topic object 330 in the topic warehouse 158 is updated with data from the newly received response capsule object 338 and saved.

The system administrator is able to access and view the contents of the command topic object 330, including the responses and attachments returned from the node 104.

In one embodiment, the system administrator initiates a series of commands to the node 104 to collect information related to status from the local agents 108, perform specific actions such as upgrading or installing software, and collecting log files indicating the results of the actions.

Example Payload Exchange

FIG. 18 through FIG. 26 provide a sequence diagram illustrating a common exchange (see also FIG. 1) of a hospital message, such as for example, an HL7 result or a lab test result, from the hospital 112 to the EMR software 122 of a primary care physician 120. In this instance, the primary care physician 120 is typically in a remote office location. In summary form, the message (a lab result in this case) flows from the hospital 112 to the agent 108a at node 104a, and the agent 108a creates a topic object 106, with the hospital node 104a and the primary care physician node 104e as participants. Once node 104e corresponding to the EMR software 122 of the primary care physician 120 is determined to be the destination node, the message is transformed into the expected format, and after several steps, the topic object 106 is streamed into a payload 280, encrypted and then uploaded from the node 104a to the rendezvous 102 where it is placed into a node queue 146 corresponding to the EMR software associated with node 104e. Then the payload is downloaded to node 104e, decrypted, and the topic object 106 is extracted as the process is reversed until finally the lab result arrives to the EMR software 122 at the primary care physician 120 remote location. An ACK is returned from the EMR software 122 to the hospital 112 in the same fashion. In between, the intelligent agents 108 at both locations have collaborated to transform the hospital generated lab result in, for example, an HL7 format to an EMR for the physician. Additionally, results from the test are tailored in a fashion that allows the primary care physician to access the information that is needed for his/her services, while safeguarding confidential or private information. Various portions of the lab result data can typically be structured in one or more topic objects, with each topic object having different groups of participants, some of which overlap while others do not. For certain type lab results, the hospital 112 and the primary care physician 120 are members of a particular participant list. For other type information, such as billing, the hospital 112, the primary care physician 120, and an insurance provider are members of another participant list. Different information can be provided to different parties from the same lab result information.

Figure 18:
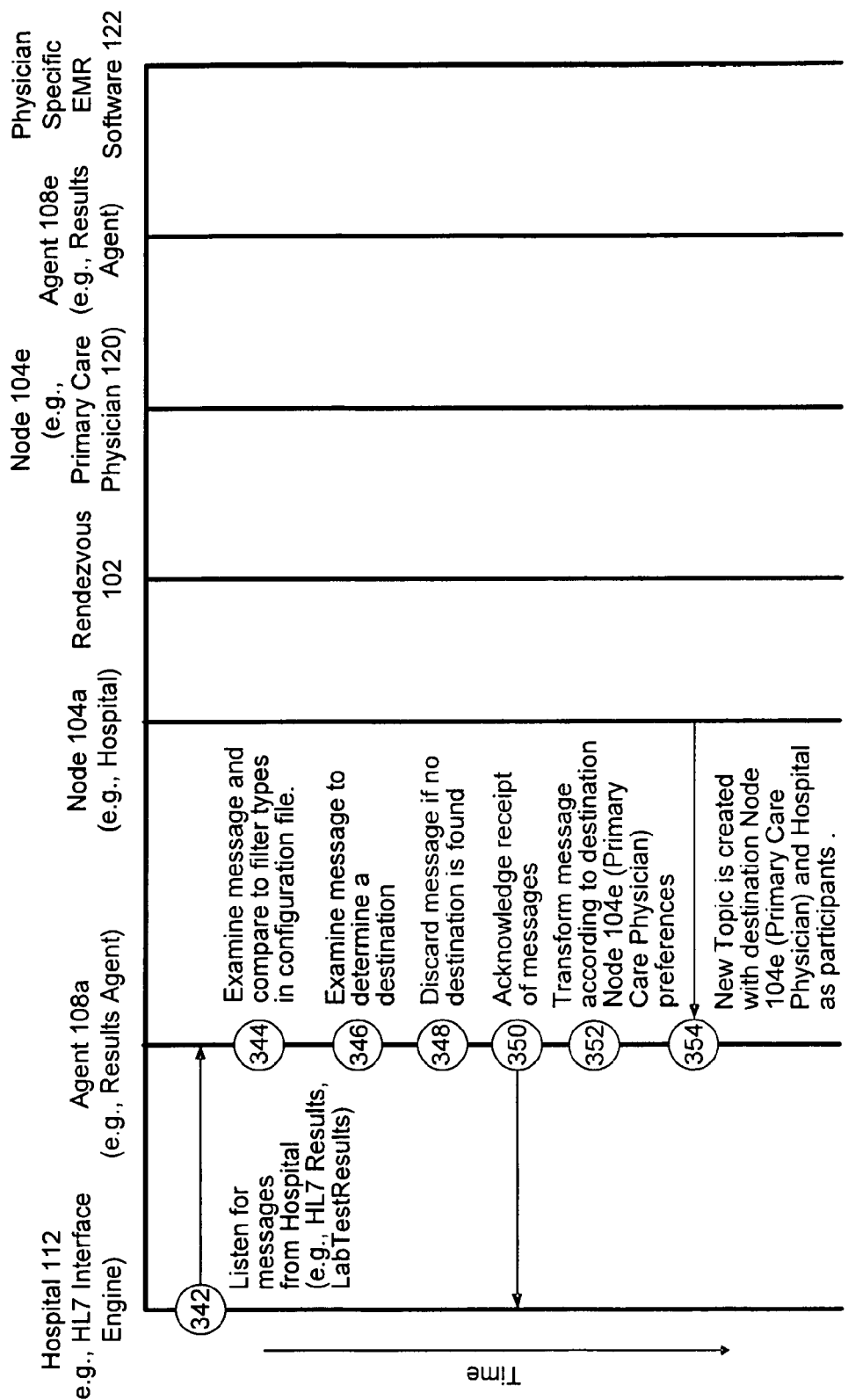
FIG. 18 is a first portion of a sequence diagram describing an example reconciliation of a clinical result between a hospital and a primary care physician according to the system of FIG. 1.
Figure 19:
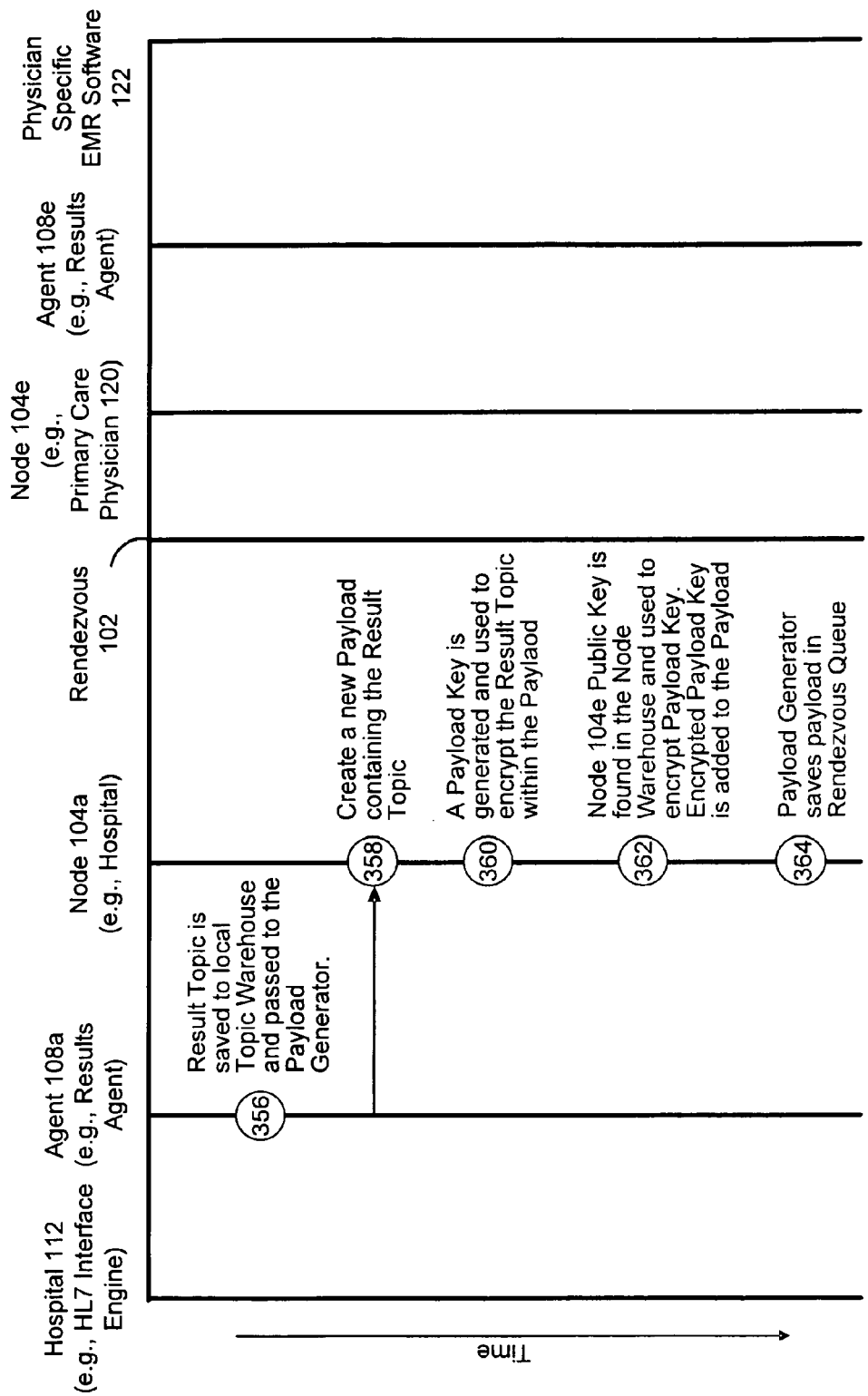
FIG. 19 is a second portion of a sequence diagram describing an example reconciliation of a clinical result between a hospital and a primary care physician according to the system of FIG. 1.
Figure 20:
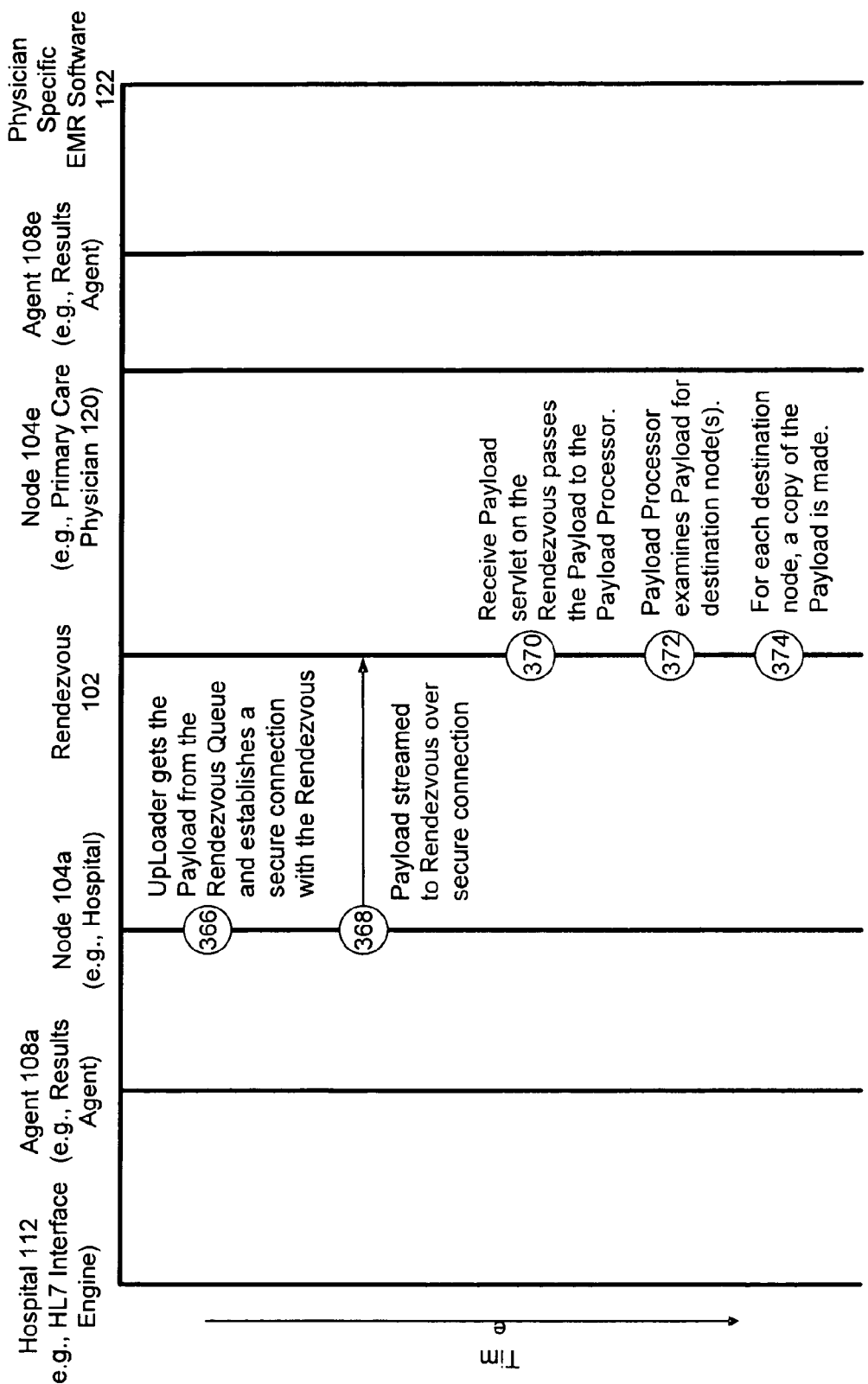
FIG. 20 is a third portion of a sequence diagram describing an example reconciliation of a clinical result between a hospital and a primary care physician according to the system of FIG. 1.
Figure 21:
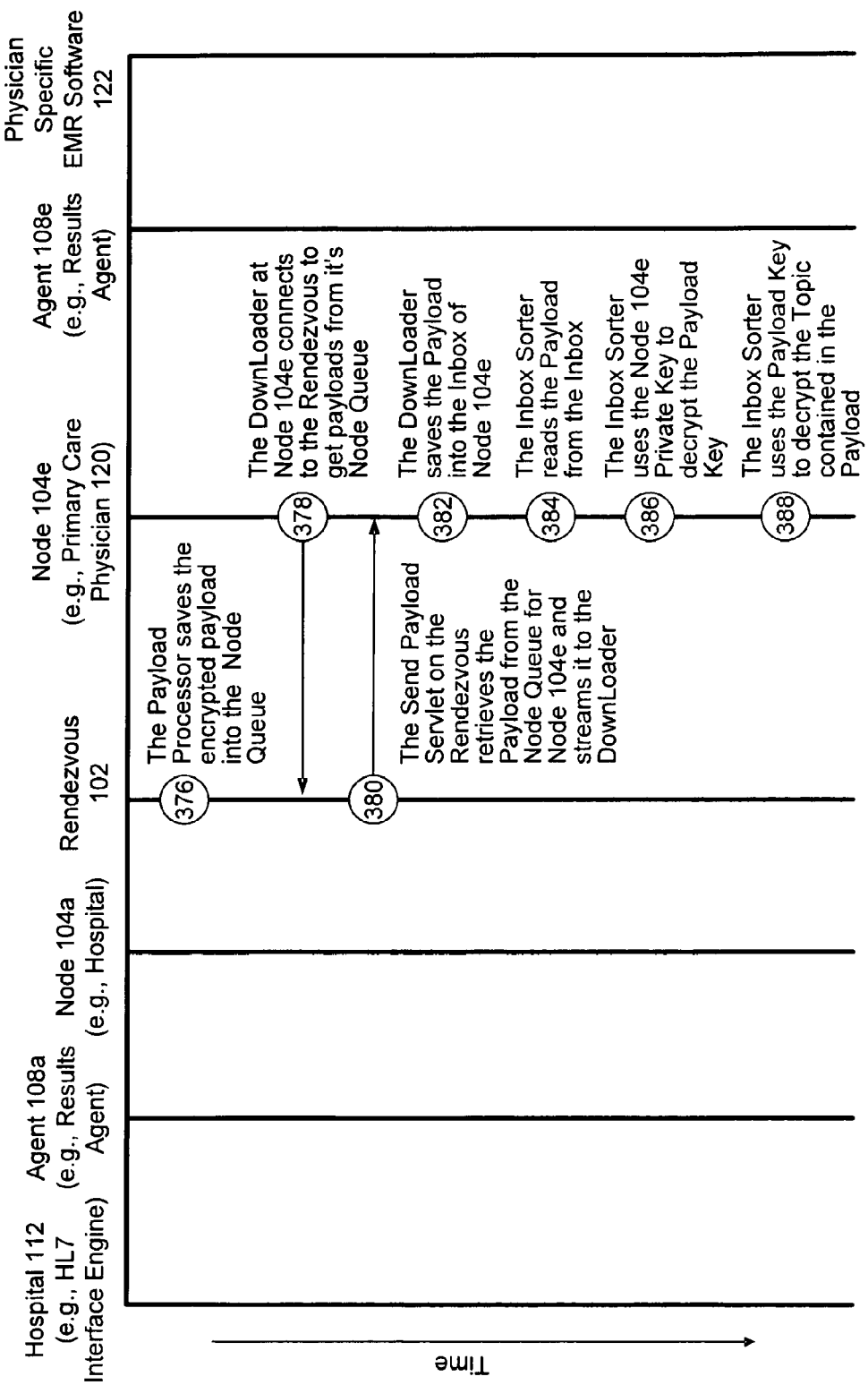
FIG. 21 is a fourth portion of a sequence diagram describing an example reconciliation of a clinical result between a hospital and a primary care physician according to the system of FIG. 1.
Figure 22:
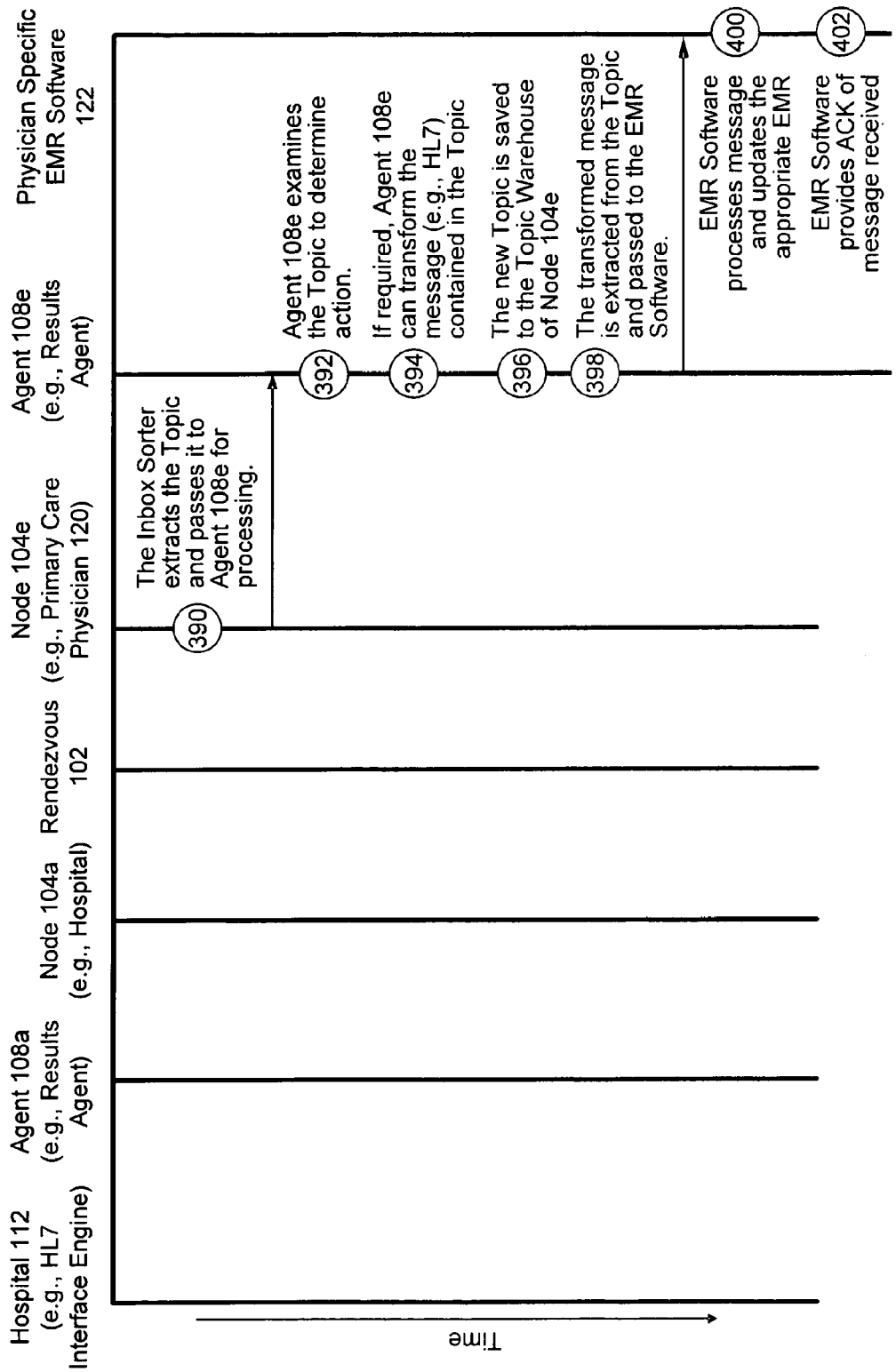
FIG. 22 is a fifth portion of a sequence diagram describing an example reconciliation of a clinical result between a hospital and a primary care physician according to the system of FIG. 1.
Figure 23:
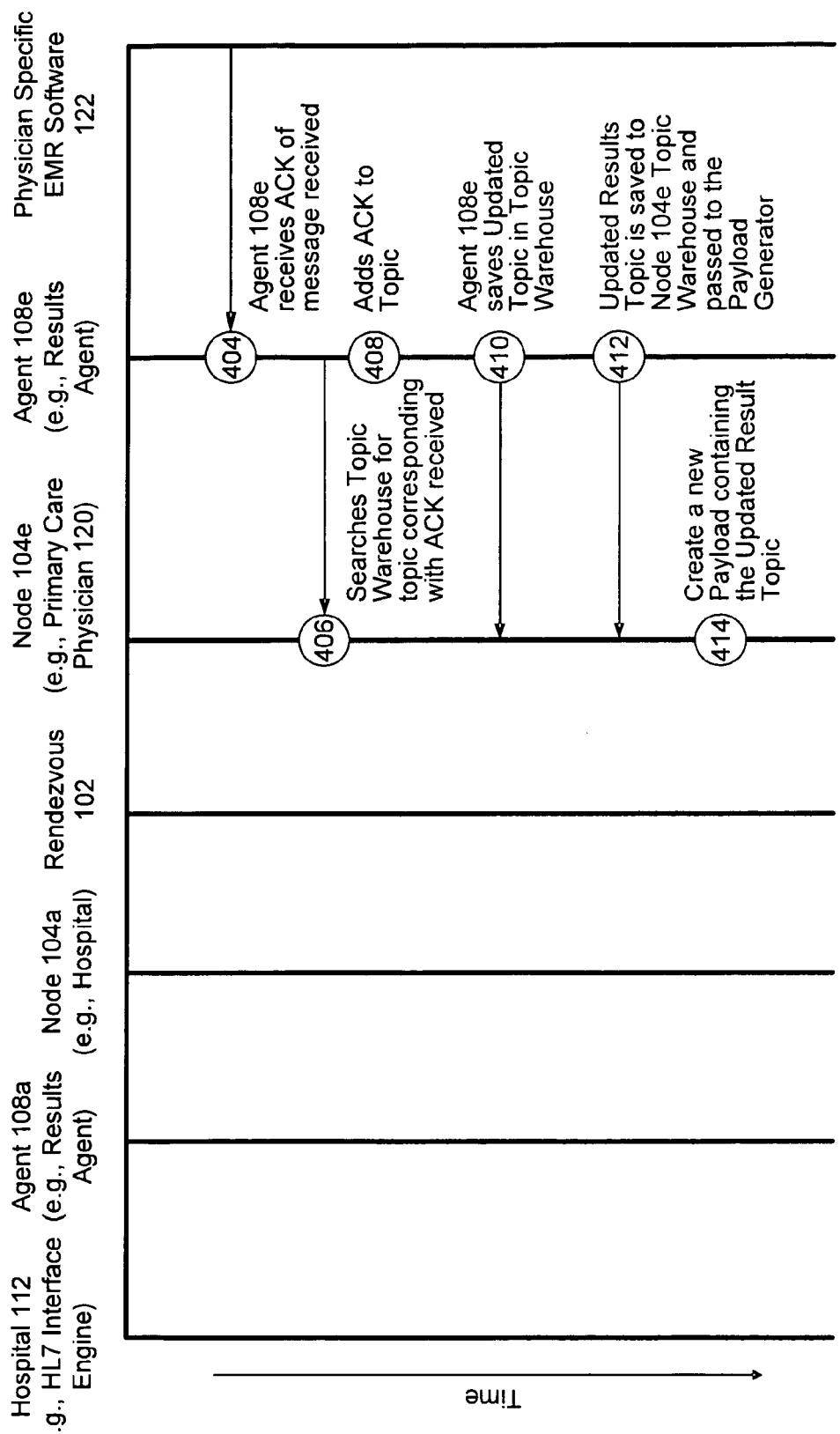
FIG. 23 is a sixth portion of a sequence diagram describing an example reconciliation of a clinical result between a hospital and a primary care physician according to the system of FIG. 1.
Figure 24:
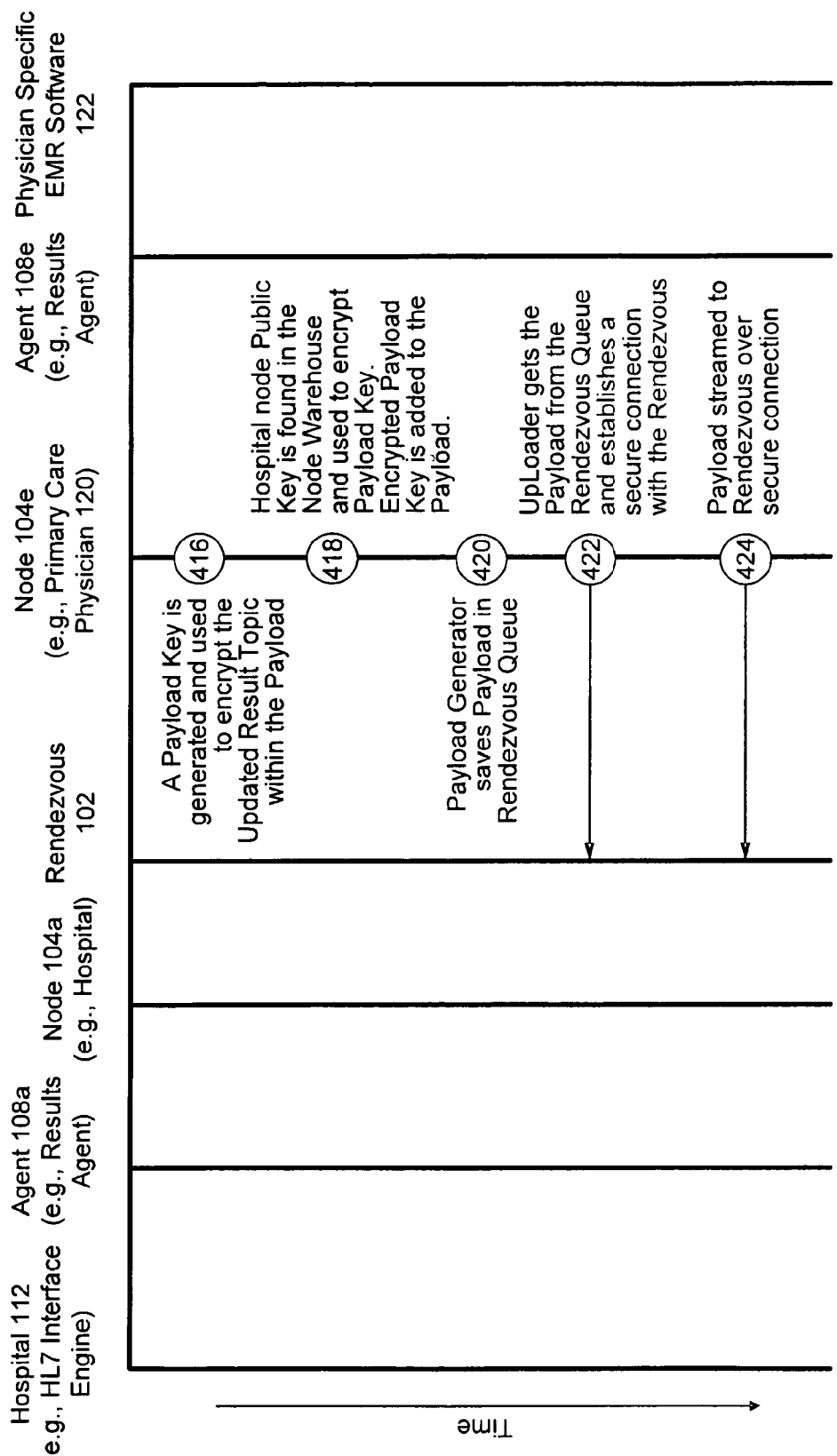
FIG. 24 is a seventh portion of a sequence diagram describing an example reconciliation of a clinical result between a hospital and a primary care physician according to the system of FIG. 1.

In FIG. 18, an intelligent agent 108a, a results agent in this case, listens for messages from the hospital 112 at step 342. When the lab test is complete and is transmitted to the agent 108a, the message is examined and compared to filter types in a configuration file at step 344. Next, at step 346, the message is examined to determine a destination node. If no destination is found, then the message is discarded at step 348. At step 350, the agent 108a acknowledges to the hospital the receipt of the message(s).

If a destination node was found, then at step 352, the agent 108a transforms the message into an appropriate format for the node 104e preferences of the primary care physician 120. An example transformation for this example is to transform an HL7 message format into an EMR format. The agent 108a then creates a new topic object 106 at step 354, with the primary care physician 120 and the hospital 112 as the participants at their respective locations, node 104e and node 104a. At step 356 (see FIG. 19), the result topic (topic object 106) is saved to a local data store such as a topic warehouse, and then passed to the payload generator 154. The local data store allows each participant node to maintain an up to date version of any topic object data that is sent by one of the other participant nodes.

After the agent 108*a* saves the result topic, the payload generator 154 at node 104*a* creates a new payload 280 at step 358. Then a payload key is generated at step 360, and used to encrypt the result topic within the payload 280. At step, 362, the public key for node 104*e* is found in the node warehouse and is used to encrypt the payload key. The encrypted payload key is also added to the payload 280. For multiple destination nodes, an encrypted payload key is added for each. At step 364, the payload generator 154 then saves the payload in the rendezvous queue 162 at node 104*a* for upload to the rendezvous 102. At step 366 (see FIG. 20), the uploader takes the payload 280 from the rendezvous queue 162 and establishes a secure connection between node 104*a* and the rendezvous 102. Then the payload 280 is streamed to the rendezvous at step 368.

The receive payload servlet 174 at the rendezvous 102 then passes the payload 280 to the payload processor 150 at step 370, where the payload processor 150 examines the payload 280 to determine destination node(s) at step 372. A copy of the payload 280 is made for each of the destination nodes in the participant list at step 374. Next, at step 376 (see FIG. 21) the payload processor 150 saves the encrypted payload 280 into the node queue 146. Upon the primary care physician 120 downloader 168 at node 104*e* connecting to the rendezvous 102 to get the payloads from its node queue 146 at step 378, the rendezvous 102 send payload servlet 176 retrieves the payload 280 from the node queue 146 corresponding to node 104*e* and streams it to the downloader 168 at step 380.

Upon receiving the payload 280 at step 382, the downloader 168 saves the payload into the inbox 164 of node 104*e*, from where the inbox sorter 160 reads the payload 280 at step 384. Then at step 386, the inbox sorter 160 uses the node 104*e* private key to decrypt the payload key. Next, the inbox sorter 160 uses the payload key to decrypt the topic contained in the payload at step 388. Then, at step 390 (see FIG. 22), the inbox sorter 160 extracts the topic and passes to the agent 108*e* for processing.

The agent 108*e* examines the topic to determine the action to take next at step 392. If required, the agent 108*e* can transform the message contained in the topic at step 394. This is useful for example, if a source node was not able to accurately perform the transformation, or if preferences have been changed or updated at the node. At step 396, the agent 108*e* saves the new topic to the topic warehouse 158 corresponding to node 104*e*. Then at step 398, the agent 108*e* extracts the transformed message from the topic and passes it to the EMR software 122.

The EMR software 122 processes the message and updates the appropriate EMR at step 400, and provides an ACK at step 402, indicating to the agent 108*e* that the message was received.

The agent 108*e* receives the ACK indicating that the message has been received at the EMR software 122, at step 404, and searches the topic warehouse 158 at node 104*e* for the topic corresponding with the received ACK at step 406. At step 408, the agent 108*e* adds the ACK to the topic, then saves the updated topic in the topic warehouse 158 at step 410. The updated results topic is also saved to the node 104*e* topic warehouse 158 and passed to the payload generator 154 at step 412.

The node 104*e* creates a new payload 280 containing the updated result topic at step 414. Then at step 416 (see FIG. 24), a payload key is generated and is used to encrypt the updated result topic within the payload 280. Next, the hospital 112 node 104*a* public key is found in the node warehouse 156 and used to encrypt the payload key at step 418. The encrypted payload key is then added to the payload 280. At step 420, the payload generator 154 saves the payload 280 in the rendezvous queue 162. Then at step 422, the uploader 166 gets the payload 280 from the rendezvous queue 162 and establishes a secure connection with the rendezvous 102, to stream the payload 280 to the rendezvous 102 over the secure connection at step 424.

Figure 25:
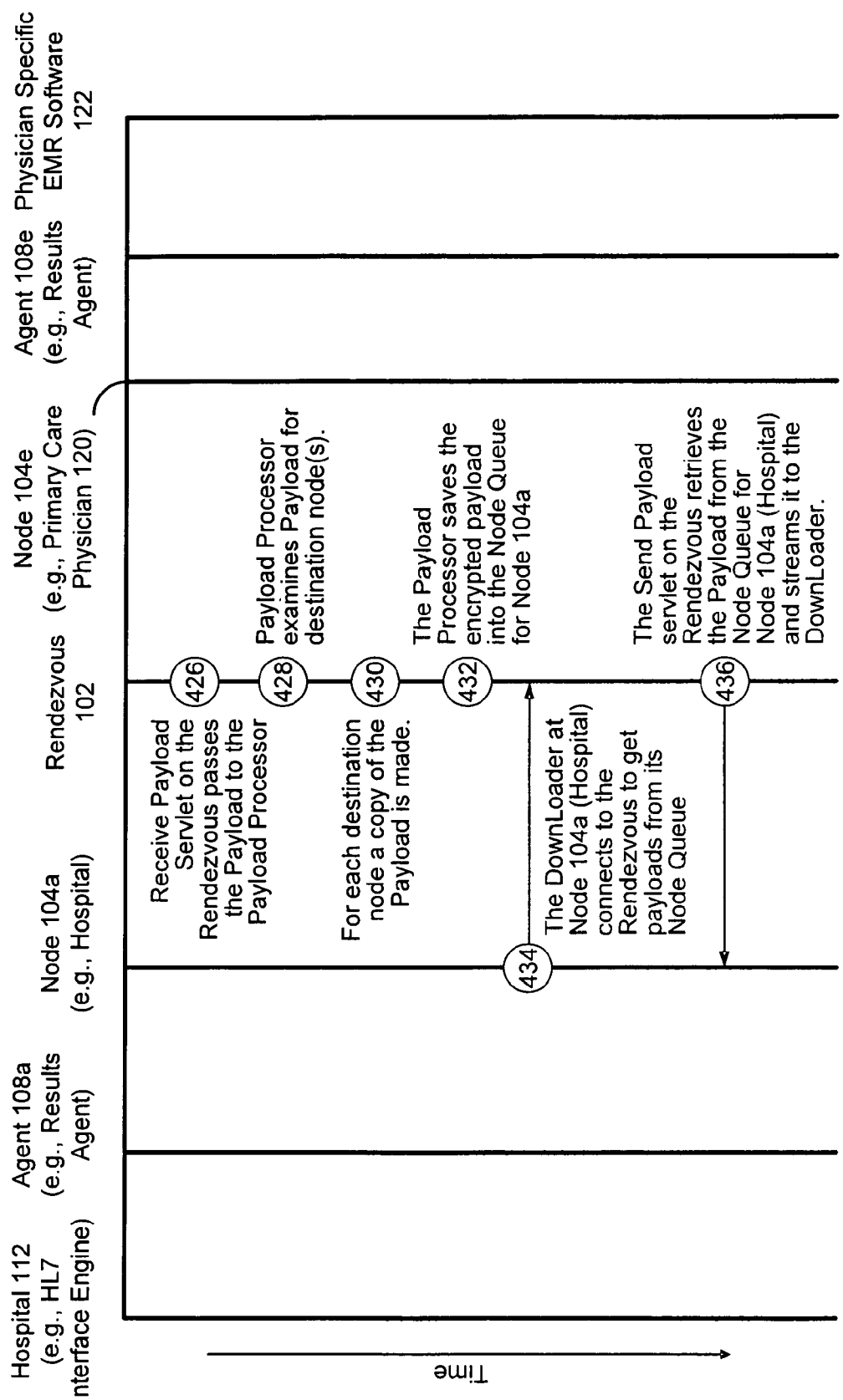
FIG. 25 is an eighth portion of a sequence diagram describing an example reconciliation of a clinical result between a hospital and a primary care physician according to the system of FIG. 1.

The receive payload servlet 174 on the rendezvous 150 passes the payload 280 to the payload processor 150 at step 426 (see FIG. 25). Upon receiving the payload 280, the payload processor 150 examines the payload 280 to determine destination node(s) at step 428. Then at step 430, a copy of the payload is made for each of the destination nodes. Next, the payload processor 150 saves the encrypted payload 280 into the node queue 146 at the rendezvous 102 that corresponds to node 104*a*. After receiving a connection from the downloader 168 at the hospital 112 node 104*a* to get payloads from its node queue 146 at step 434, the send payload servlet 176 on the rendezvous 102 retrieves the payload 280 from the node queue 146 for node 104*a* and streams it to the downloader 168 at step 436.

Figure 26:
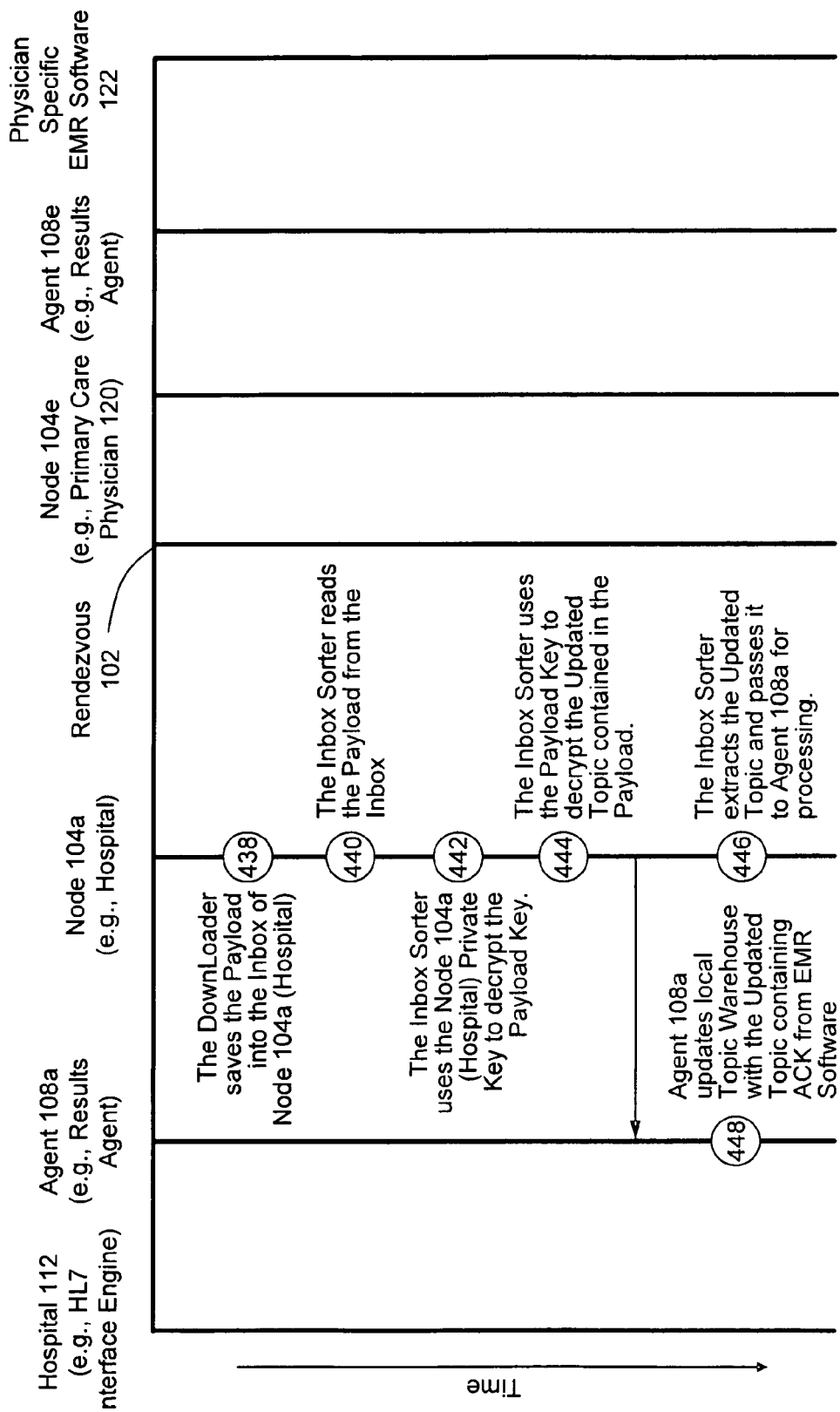
FIG. 26 is a final portion of a sequence diagram describing an example reconciliation of a clinical result between a hospital and a primary care physician according to the system of FIG. 1.

At the hospital 112 node 104*a*, the downloader 168 saves the payload 280 into the inbox 164 at step 438 (see FIG. 26). The inbox sorter 160 reads the payload 280 from the inbox 164 at step 440. Then at step 442, the inbox sorter 160 uses the node 104*a* private key to decrypt the payload key, and then at step 444, uses the payload key to decrypt the updated topic contained in the payload 280. The inbox sorter 160 extracts the updated topic and passes it to agent 108*a* for processing at step 446. Finally, at step 448 the agent 108*a* updates the local topic warehouse 158 with the updated topic containing the ACK from the EMR software 122 and the communication is complete.

Both agents 108 have been provided with updates as to the contents of the topic at the other agent 108 and given an opportunity to update the corresponding portions accordingly.

Accordingly, it will be understood that various embodiments of the present invention described herein are preferably implemented as a special purpose or general-purpose computer including various computer hardware as discussed in greater detail below. Embodiments within the scope of the present invention also include computer-readable media for carrying or having computer-executable instructions or data structures stored thereon. Such computer-readable media can be any available media which can be accessed by a general purpose or special purpose computer, or downloadable to through wireless communication networks. By way of example, and not limitation, such computer-readable media can comprise physical storage media such as RAM, ROM, flash memory, EEPROM, CD-ROM, DVD, or other optical disk storage, magnetic disk storage or other magnetic storage devices, any type of removable non-volatile memories such as secure digital (SD), flash memory, memory stick etc., or any other medium which can be used to carry or store computer program code in the form of computer-executable instructions or data structures and which can be accessed by a general purpose or special purpose computer, or a mobile device.

When information is transferred or provided over a network or another communications connection (either hardwired, wireless, or a combination of hardwired or wireless) to a computer, the computer properly views the connection as a computer-readable medium. Thus, any such a connection is properly termed and considered a computer-readable medium. Combinations of the above should also be included within the scope of computer-readable media. Computer-executable instructions comprise, for example, instructions and data which cause a general purpose computer, special purpose computer, or special purpose processing device such as a mobile device processor to perform one specific function or a group of functions.

Those skilled in the art will understand the features and aspects of a suitable computing environment in which aspects of the invention may be implemented. Although not required, the inventions will be described in the general context of computer-executable instructions, such as program modules, being executed by computers in networked environments. Such program modules are often reflected and illustrated by flow charts, sequence diagrams, exemplary screen displays, and other techniques used by those skilled in the art to communicate how to make and use such computer program modules. Generally, program modules include routines, programs, objects, components, data structures, etc. that perform particular tasks or implement particular abstract data types, within the computer. Computer-executable instructions, associated data structures, and program modules represent examples of the program code for executing steps of the methods disclosed herein. The particular sequence of such executable instructions or associated data structures represent examples of corresponding acts for implementing the functions described in such steps.

Those skilled in the art will also appreciate that the invention may be practiced in network computing environments with many types of computer system configurations, including personal computers, hand-held devices, multi-processor systems, microprocessor-based or programmable consumer electronics, networked PCs, minicomputers, mainframe computers, and the like. The invention may also be practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

An exemplary system for implementing the inventions, which is not illustrated, includes a general purpose computing device in the form of a conventional computer, including a processing unit, a system memory, and a system bus that couples various system components including the system memory to the processing unit. The computer will typically include one or more magnetic hard disk drives (also called "data stores" or "data storage" or other names) for reading from and writing to. The drives and their associated computer-readable media provide nonvolatile storage of computer-executable instructions, data structures, program modules, and other data for the computer. Although the exemplary environment described herein employs a magnetic hard disk, a removable magnetic disk, removable optical disks, other types of computer readable media for storing data can be used, including magnetic cassettes, flash memory cards, digital video disks (DVDs), Bernoulli cartridges, RAMS, ROMs, and the like.

Computer program code that implements most of the functionality described herein typically comprises one or more program modules may be stored on the hard disk or other storage medium. This program code, as is known to those skilled in the art, usually includes an operating system, one or more application programs, other program modules, and program data. A user may enter commands and information into the computer through keyboard, pointing device, or other input devices (not shown), such as a microphone, game pad, satellite dish, scanner, or the like. These and other input devices are often connected to the processing unit through known electrical, optical, or wireless connections.

The main computer that effects many aspects of the inventions will typically operate in a networked environment using logical connections to one or more remote computers or data sources, which are described further below. Remote computers may be another personal computer, a server, a router, a network PC, a peer device or other common network node, and typically include many or all of the elements described above relative to the main computer system in which the inventions are embodied. The logical connections between computers include a local area network (LAN), a wide area network (WAN), and wireless LANs (WLAN) that are presented here by way of example and not limitation. Such networking environments are commonplace in office-wide or enterprise-wide computer networks, intranets and the Internet.

When used in a LAN or WLAN networking environment, the main computer system implementing aspects of the invention is connected to the local network through a network interface or adapter. When used in a WAN or WLAN networking environment, the computer may include a modem, a wireless link, or other means for establishing communications over the wide area network, such as the Internet. In a networked environment, program modules depicted relative to the computer, or portions thereof, may be stored in a remote memory storage device. It will be appreciated that the network connections described or shown are exemplary and other means of establishing communications over wide area networks or the Internet may be used.

In view of the foregoing detailed description of preferred embodiments of the present invention, it readily will be understood by those persons skilled in the art that the present invention is susceptible to broad utility and application. While various aspects have been described in the context of a preferred embodiment, additional aspects, features, and methodologies of the present invention will be readily discernable therefrom. Many embodiments and adaptations of the present invention other than those herein described, as well as many variations, modifications, and equivalent arrangements and methodologies, will be apparent from or reasonably suggested by the present invention and the foregoing description thereof, without departing from the substance or scope of the present invention. Furthermore, any sequence(s) and/or temporal order of steps of various processes described and claimed herein are those considered to be the best mode contemplated for carrying out the present invention. It should also be understood that, although steps of various processes may be shown and described as being in a preferred sequence or temporal order, the steps of any such processes are not limited to being carried out in any particular sequence or order, absent a specific indication of such to achieve a particular intended result. In most cases, the steps of such processes may be carried out in a variety of different sequences and orders, while still falling within the scope of the present inventions. In addition, some steps may be carried out simultaneously. Accordingly, while the present invention has been described herein in detail in relation to preferred embodiments, it is to be understood that this disclosure is only illustrative and exemplary of the present invention and is made merely for purposes of providing a full and enabling disclosure of the invention. The foregoing disclosure is not intended nor is to be construed to limit the present invention or otherwise to exclude any such other embodiments, adap- Therefore, having thus described the invention, at least the following is claimed:

1. A system for distributing healthcare data from a source node to one or more destination nodes selectable from one or more distributed computing nodes on a data communication network exchanging healthcare information, the system comprising:
  a source node that receives healthcare information, the source node comprising:
    an agent configured to analyze the healthcare information and generate a topic including the healthcare information and a list of participating nodes determined from the healthcare information, the topic relating to an electronic medical record and being one of the following groups: a results topic, a provider topic and a physician office definition topic;
    a payload generator configured to create a payload for distribution of the healthcare information, wherein the payload comprises the topic and a destination node list identifying the list of participating nodes; and
    an upload module configured for sending the payload to a rendezvous server;
  the rendezvous server comprising:
    a plurality of destination node queues corresponding to separate destination nodes; and
    a rendezvous payload processor configured to receive the payload from the upload module, to retrieve at least one destination node from the destination node list and to place a copy of the payload into at least one destination node queue, each destination node queue corresponding to a respective destination node from the destination node list;
  the at least one destination node, each destination node comprising:
    a download module configured to download the payload from the destination node queue corresponding to the destination node upon determination that the rendezvous server contains the payload;
    an inbox module configured to receive the payload from the download module;
    an inbox sort module configured to extract the topic from the payload; and
    an intelligent agent configured to receive the healthcare information included in the topic from the inbox sort module and utilize the healthcare information included in the topic according to destination node requirements.

2. The system of claim 1, the intelligent agent further configured to process healthcare information from the topic and secondary changes associated with the destination node, and to generate secondary healthcare information corresponding to the secondary changes.

3. The system of claim 2, the destination node further comprising a second payload generator configured to create a second payload, the second payload comprising the secondary healthcare information and the destination node list.

4. The system of claim 3, the destination node further comprising a rendezvous queue for short term storage of the second payload.

5. The system of claim 4, the destination node further comprising a second upload module configured for sending the second payload to the rendezvous payload processor upon determination that the rendezvous queue contains the second payload.

6. The system of claim 5, the rendezvous payload processor further configured to receive the second payload from the second upload module, to retrieve at least one destination node from the destination node list and to place a copy of the second payload in the at least one destination node queue, each destination node queue corresponding to a respective destination node.

7. The system of claim 6, the source node further comprising a second download module configured to download the second payload from the destination node queue corresponding to the source node upon determination that the rendezvous server contains the second payload.

8. The system of claim 7, the source node further comprising a source inbox module to receive the second payload from the second download module.

9. The system of claim 8, the source node further comprising a source inbox sort module configured to extract secondary information from the second payload in the source inbox module and decrypt the secondary information.

10. The system of claim 9, the source node further configured to receive the secondary information from the source inbox sort module and utilize the secondary information according to source node requirements.

11. The system of claim 1, wherein the healthcare information is received as an HL7 message and processed at the source node to provide a results topic object.

12. The system of claim 1, wherein the payload comprises a unique payload identifier (ID), a payload type identifier (ID), the destination node list, a processor identifier (ID), a payload key, and the topic.

13. The system of claim 12, wherein the payload ID is used by the rendezvous payload processor to manage and sort payloads.

14. The system of claim 12, wherein the payload type ID indicates a value selectable from: topic payload, capsule payload, command payload, and management payload.

15. The system of claim 12, wherein the processor ID indicates a name of an application for processing the payload.

16. The system of claim 12, wherein the payload key comprises a security key involved in an encryption and/or decryption of the payload.

17. The system of claim 1, wherein the destination node requirements include a synchronization and/or update of particular information from the source node to corresponding information at the destination node.

18. The system of claim 1, wherein the destination node requirements include a receipt of new information from the source node in a new topic object.

19. The system of claim 1, wherein the healthcare information comprises difference data associated with the source node relative to data at a destination node, and wherein specified portions of the destination node data are reconciled with corresponding portions of source node data.

20. The system of claim 1, wherein the healthcare information received at the source node is HL7 information, and wherein the source node processes the HL7 information prior to forming the payload by one or more of the following operations:
  (1) mapping data from one format to another,
  (2) adding information not present in the original HL7 information,
  (3) removing or modifying data from the original HL7 information, and (4) discarding duplicates and/or acting on changes in status.

21. The system of claim 1, wherein the intelligent agent is further configured to utilize the list of participating nodes included in the topic according to the destination node requirements.

22. A computer method for distributing healthcare data from a source node to one or more destination nodes selectable from multiple distributed computing nodes on a data communication network exchanging healthcare information the method comprising the steps of:
at the source node, in response to receipt of healthcare information putting the healthcare information into a topic object, the topic object relating to an electronic medical record and being one of the following groups: a results topic object, a provider topic object and a physician office definition topic object;
defining a topic participant list including at least one destination node related to the topic object and determined from the healthcare information, wherein the at least one destination node is authorized to access the healthcare information in the topic object;
encapsulating the topic participant list into the topic object;
storing the topic object at the source node;
encapsulating the topic object and a destination node list identifying the topic participant list into a payload;
sending the payload to a rendezvous server;
at the rendezvous server, receiving the payload and retrieving at least one destination node from the destination node list, the rendezvous server having a plurality of destination node queues corresponding to separate destination nodes;
placing a copy of the payload into at least one destination node queue, each destination node queue corresponding to a respective node from the destination node list;
at the at least one destination node, downloading the payload from the destination node queue corresponding to the destination node upon determination that the rendezvous server contains the payload; and
at the at least one destination node, extracting the topic object from the payload and utilizing the healthcare information in the topic object, according to topic object requirements.

23. The method of claim 22, wherein the healthcare information is received as an HL7 message and processed at the source node to provide the results topic object.

24. The method of claim 22, wherein the topic object includes a unique payload identifier (ID), a payload type identifier (ID), the destination node list, a processor identifier (ID), a payload key, and topic data.

25. The method of claim 24, wherein the payload ID is used by a rendezvous payload processor to manage and sort payloads.

26. The method of claim 24, wherein the payload type ID indicates a value selectable from: a topic payload, a capsule payload, a command payload, and a management payload.

27. The method of claim 24, wherein the processor (ID) indicates a name of an application for processing the topic object.

28. The method of claim 24, wherein the payload key comprises a security key involved in an encryption and/or decryption of the topic object.

29. The method of claim 22, wherein the topic object requirements include the synchronization and/or update of particular information from the source node to corresponding information at the destination node.

30. The method of claim 22, wherein the topic object requirements include the receipt of new information from the source node in a new topic object.

31. The method of claim 22, wherein the healthcare information comprises difference data associated with the source node relative to data at a destination node, and wherein specified portions of the destination node data are reconciled with corresponding portions of source node data.

32. The method of claim 22, wherein the healthcare information received at the source node is HL7 information, and further comprising the step of processing the HL7 information prior to forming the topic object by one or more of the following operations:
(1) mapping data from one format to another,
(2) adding information not present in the original HL7 information,
(3) removing or modifying data from the original HL7 information, and
(4) discarding duplicates and/or acting on changes in status.

33. A system for distributing healthcare data from a source node to one or more destination nodes selectable from multiple distributed computing nodes on a data communication network exchanging healthcare information, the system comprising:
the source node that receives the healthcare information;
a rendezvous server having at least one destination node queue;
at least one destination node; and
a local data store,
wherein the source node is configured for:
encapsulating the healthcare information and a topic participant list identifying at least one destination node determined from the healthcare information into at least one topic object, the topic object relating to an electronic medical record and being one of the following groups: a results topic object, a provider topic object and a physician office definition topic object;
storing the at least one topic object in the local data store;
encapsulating the at least one topic object and a destination node list identifying the topic participant list into a payload, the payload including a payload ID, a payload type ID and the topic object;
encrypting the payload; and
sending the payload to the rendezvous server;
wherein the rendezvous server is configured for:
receiving the payload;
retrieving the at least one destination node from the topic participant list; and
placing a copy of the payload into the at least one destination node queue identified in the topic participant list; and
wherein each destination node is configured for:
retrieving the payload from the corresponding destination node queue upon determination that the rendezvous server contains the payload;
decrypting the payload;
upon a determination that the destination node is included in the topic participant list, extracting the topic object from the payload; and
utilizing the healthcare information in the topic object according to topic object requirements at the destination node.

34. The system of claim 33, wherein the local data store is at the source node for maintaining the at least one topic object.

35. The system of claim 34, wherein the local data store is a topic warehouse.

36. The system of claim 33, further comprising at least one local data store at each destination node for maintaining each topic object.

37. The system of claim 33, wherein each destination node is further configured to reconcile at least one specified portion of preexisting predetermined health information at the destination node with updated healthcare information from the source node.

38. The system of claim 33, wherein the at least one destination node is located remotely from the source node.

39. The system of claim 38, wherein the topic participant list excludes at least one remotely located destination node.

40. The system of claim 33, wherein the healthcare information is received as an HL7 message and processed at the source node to provide the results topic object.

41. The system of claim 33, wherein the payload ID is used to manage and sort payloads.

42. The system of claim 33, wherein the payload type ID indicates a value selectable from: a topic payload, a capsule payload, a command payload, and a management payload.

43. The system of claim 33, wherein the topic object further includes a processor identifier (ID), a payload key, and topic data.

44. The system of claim 43, wherein the processor ID is used to indicate a name of an application for processing the topic object.

45. The system of claim 43, wherein the payload key is involved in the encrypting and/or decrypting the topic object.

46. The system of claim 33, wherein the topic object requirements include the synchronization and/or update of particular information from the source node to corresponding information at the destination node.

47. The system of claim 33, wherein the topic object requirements include a receipt of new information from the source node in a new topic object.

48. The system of claim 33, wherein the healthcare information comprises difference data associated with the source node relative to data at a destination node, and wherein specified portions of the destination node data arc reconciled with corresponding portions of source node data.

49. The system of claim 33, wherein the healthcare information received at the source node is HL7 information, and further comprising the step of processing the HL7 information prior to forming the topic object by one or more of the following operations:
  (1) mapping data from one format to another,
  (2) adding information not present in the original HL7 information,
  (3) removing or modifying data from the original HL7 information, and
  (4) discarding duplicates and/or acting on changes in status.

* * * * *